(12) United States Patent
Hirohara et al.

(10) Patent No.: US 6,629,761 B1
(45) Date of Patent: Oct. 7, 2003

(54) EYE CHARACTERISTIC MEASURING APPARATUS

(75) Inventors: Yoko Hirohara, Tokyo (JP); Toshifumi Mihashi, Tokyo (JP); Yasufumi Fukuma, Tokyo (JP)

(73) Assignee: Kabushiki Kaisha Topcon, Tokyo (JP)

( * ) Notice: Subject to any disclaimer, the term of this patent is extended or adjusted under 35 U.S.C. 154(b) by 0 days.

(21) Appl. No.: 09/713,790

(22) Filed: Nov. 15, 2000

(30) Foreign Application Priority Data

Nov. 15, 1999 (JP) .......................................... 11-324744
Oct. 18, 2000 (JP) ...................................... 2000-318640
Oct. 20, 2000 (JP) ...................................... 2000-321509

(51) Int. Cl.$^7$ ................................................. A61B 3/10
(52) U.S. Cl. ...................................................... 351/221
(58) Field of Search ................................ 351/200, 205, 351/206, 213, 215, 216, 221, 246; 600/558

(56) References Cited

U.S. PATENT DOCUMENTS 4,436,388 A * 3/1984 Takahashi et al. .......... 351/206
6,234,978 B1 * 5/2001 Mihashi et al. ............. 600/558
6,273,566 B1 * 8/2001 Kobayashi et al. ......... 351/221

* cited by examiner

Primary Examiner—Marvin M. Lateef
Assistant Examiner—John R. Sanders
(74) Attorney, Agent, or Firm—Baker Botts LLP

(57) ABSTRACT

The present invention provides an eye characteristic measuring apparatus provided with an image forming condition changing unit for achieving an appropriate illuminating condition and capable of setting an optimum illuminating condition and an optimum light receiving condition. A first light source emits light, a first illuminating optical system illuminates a small region of the retina of the eye with the light emitted by the first illuminating optical system in a variable illuminating condition, a first photodetecting optical system guides part of reflected light reflected from the retina of the eye through a first transforming device that divides the reflected light into at least seventeen light beams to a first photodetecting device, an arithmetic unit determines the optical characteristic of the eye on the basis of a first signal provided by the first photodetecting device and corresponding to the inclination of light, and an image forming condition changing unit changes the respectively image forming conditions of the first illuminating optical system and the first photodetecting optical system.

19 Claims, 32 Drawing Sheets

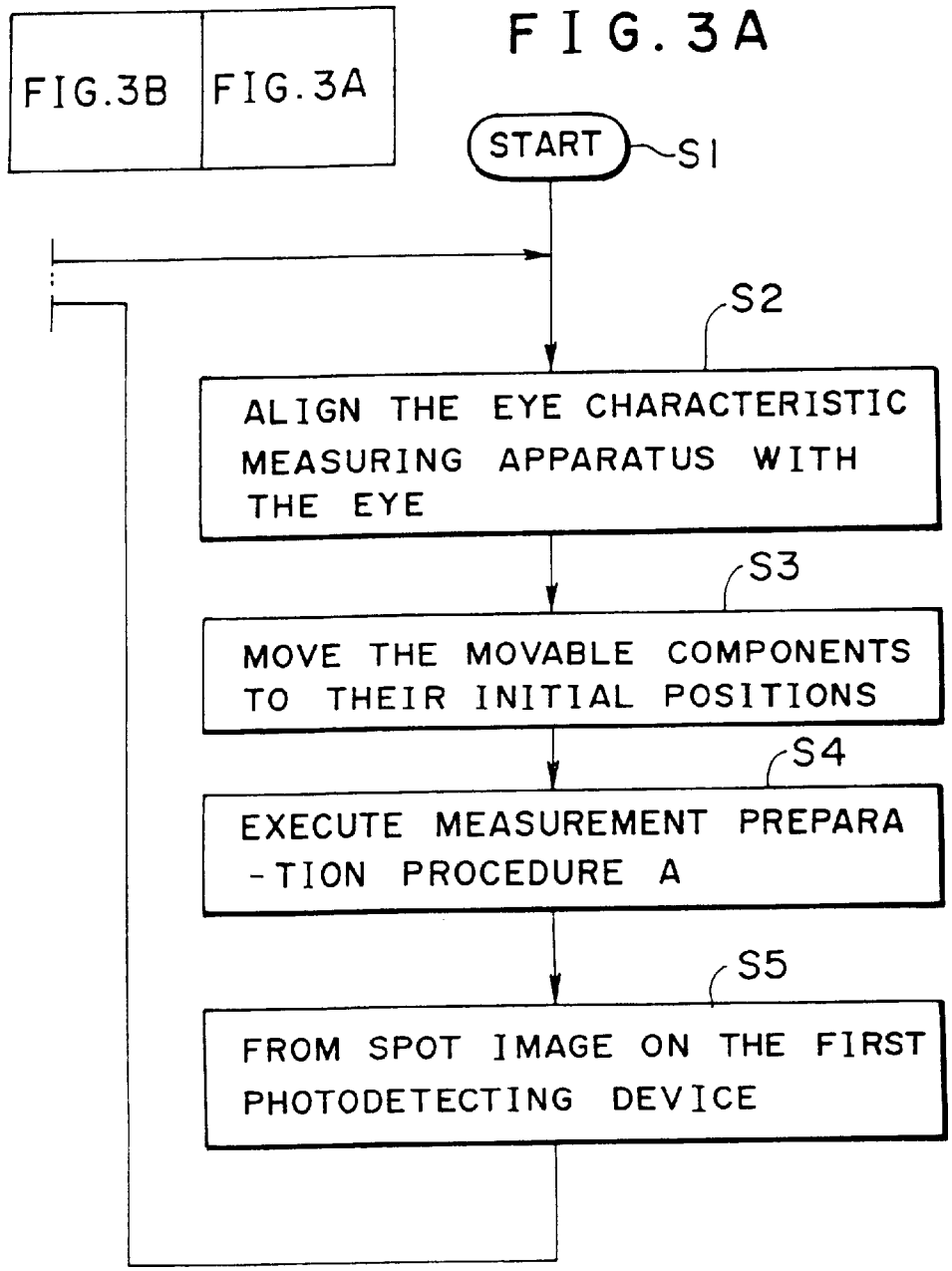

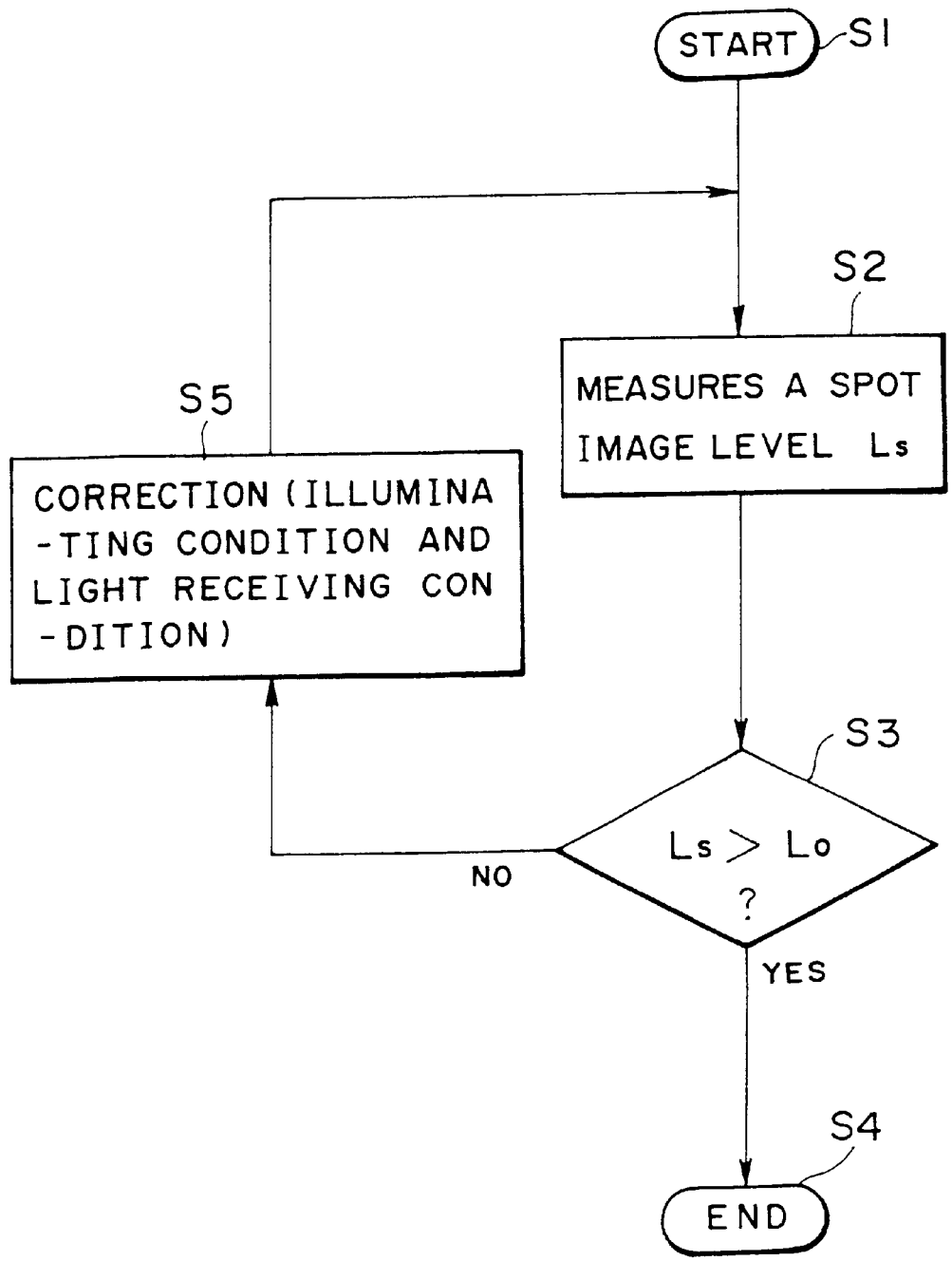

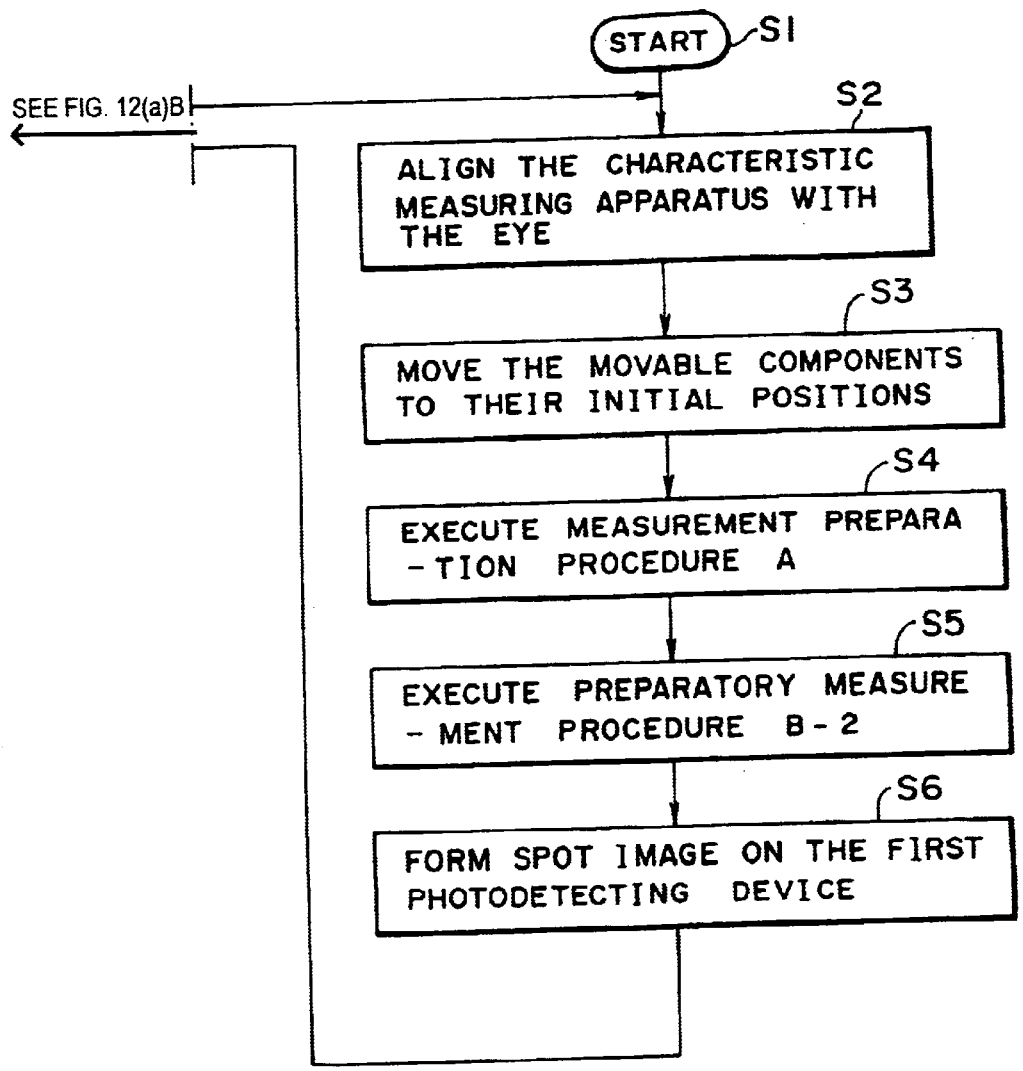
FIG. 12(a)A

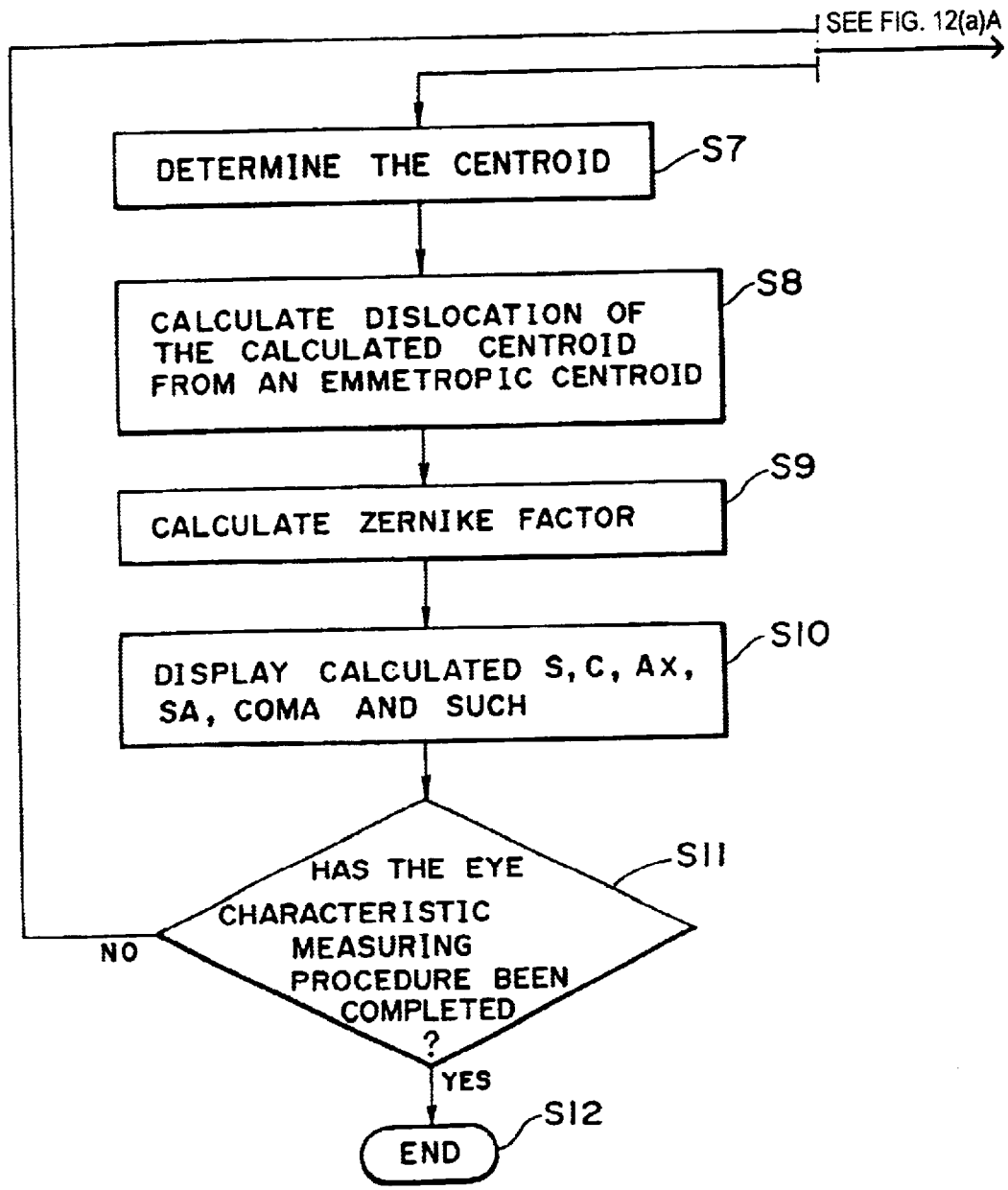
FIG. 12(a)B

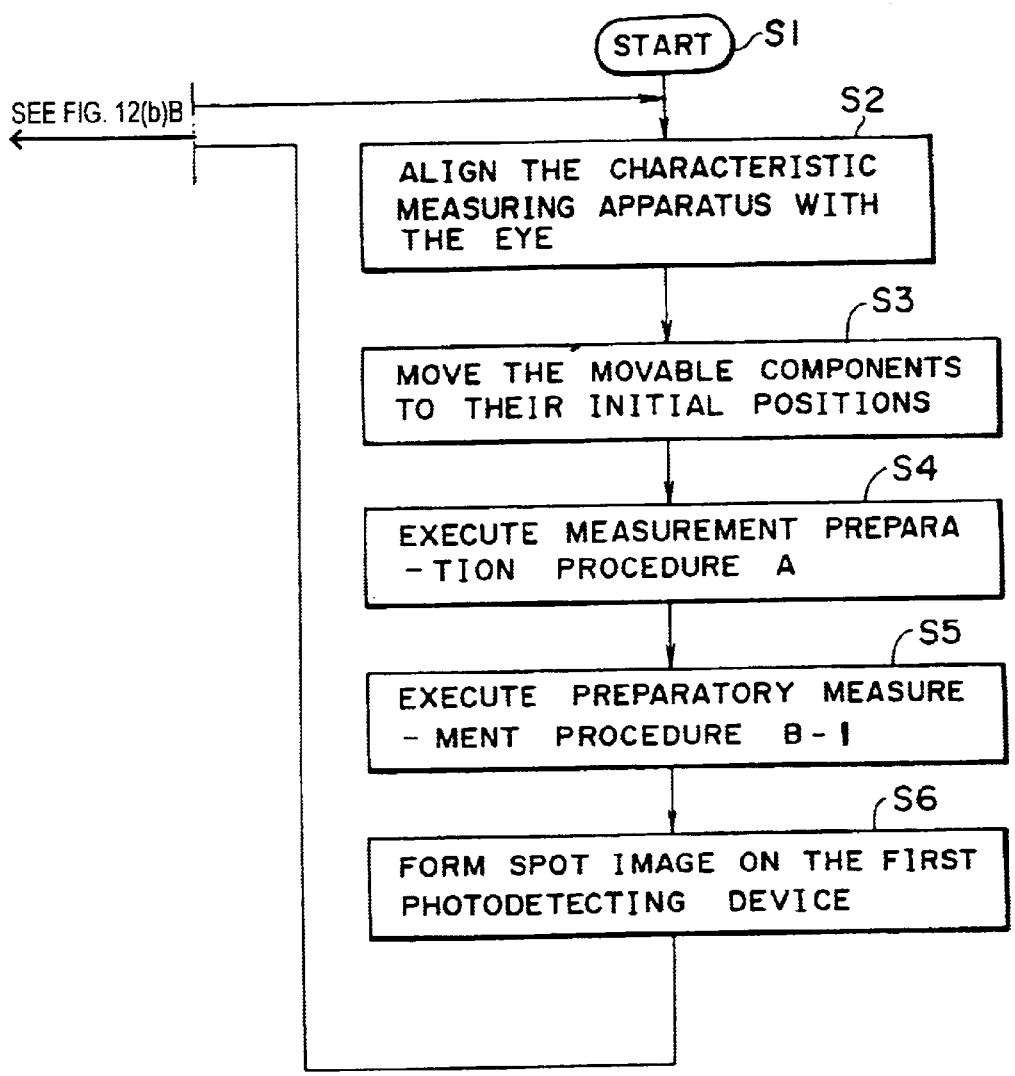
FIG. 12(b)A

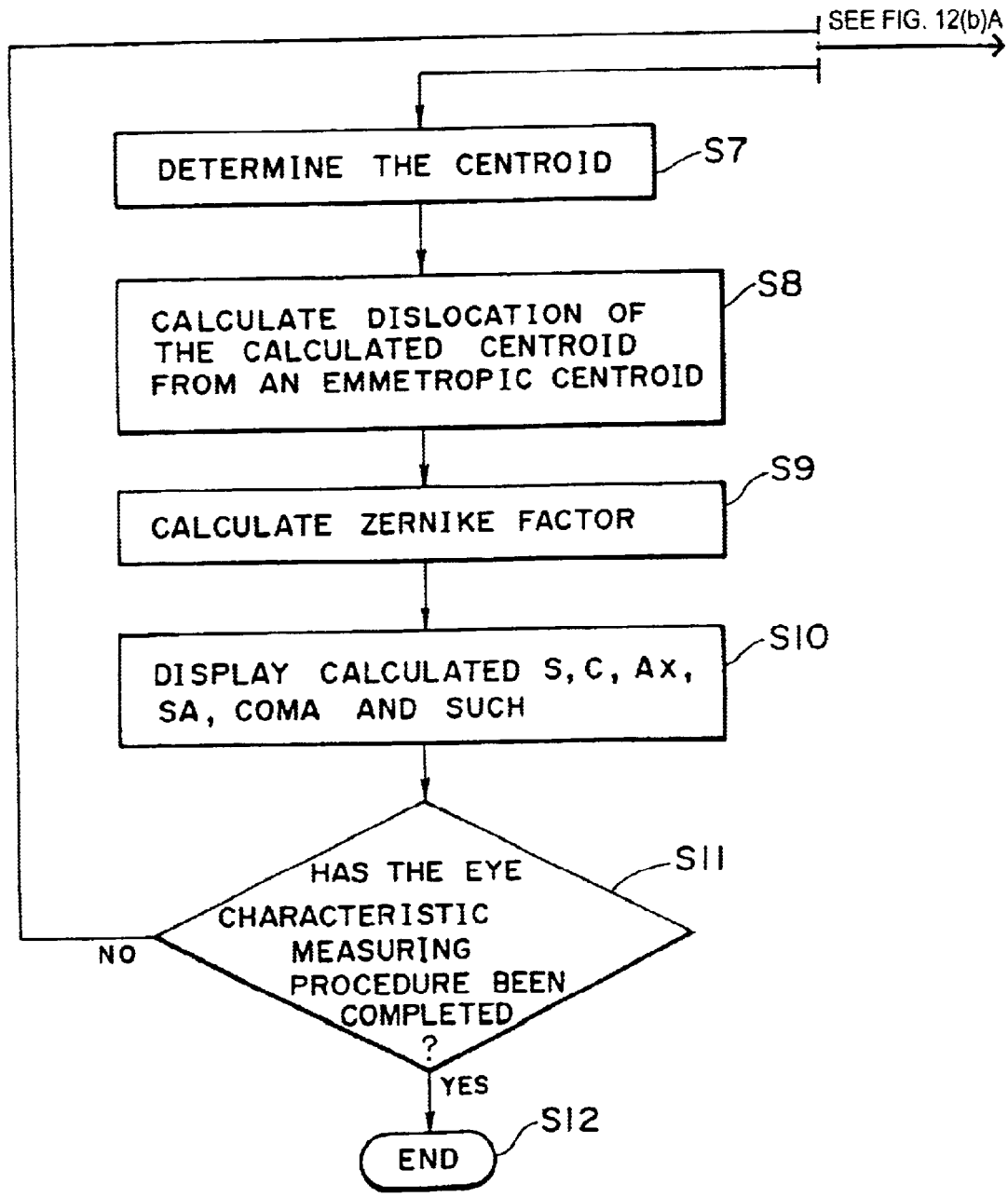
FIG. 12(b)B

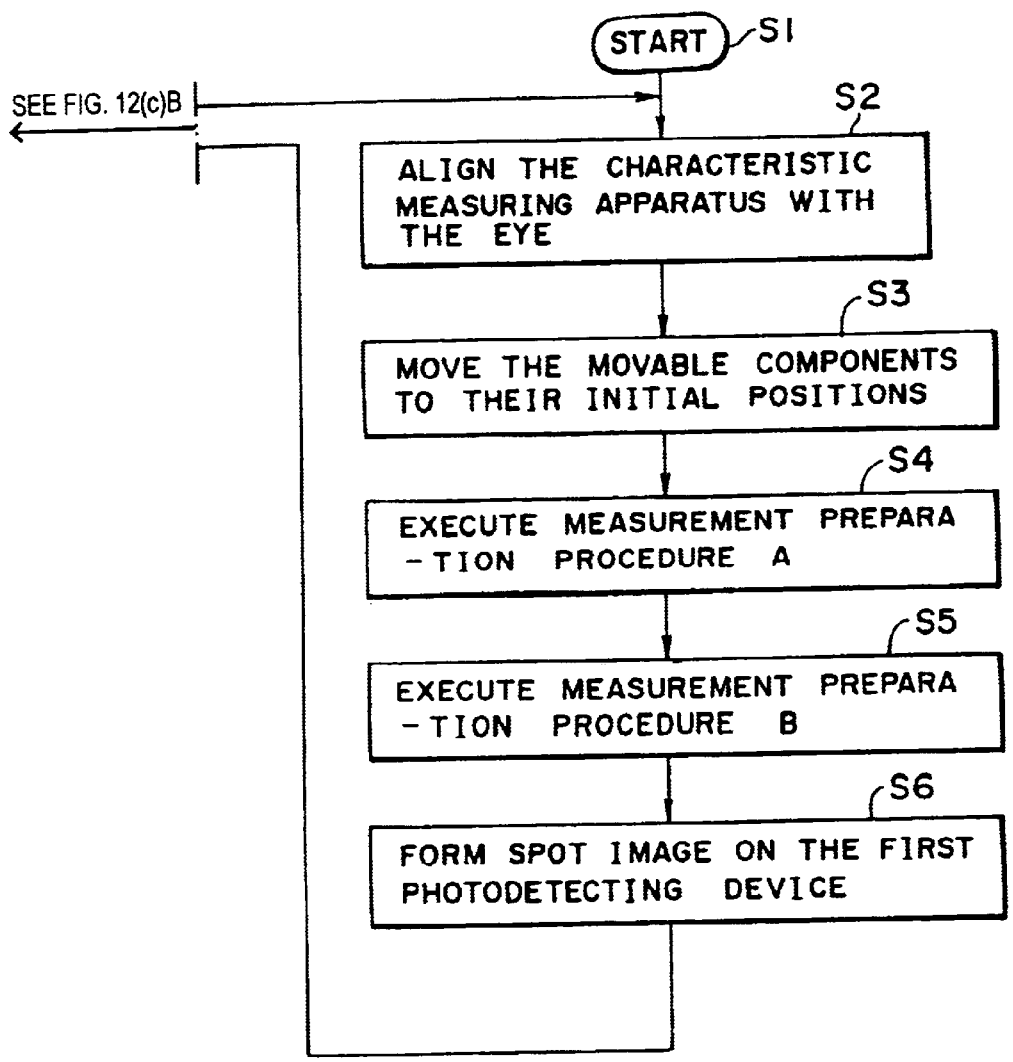
FIG. 12(c)A

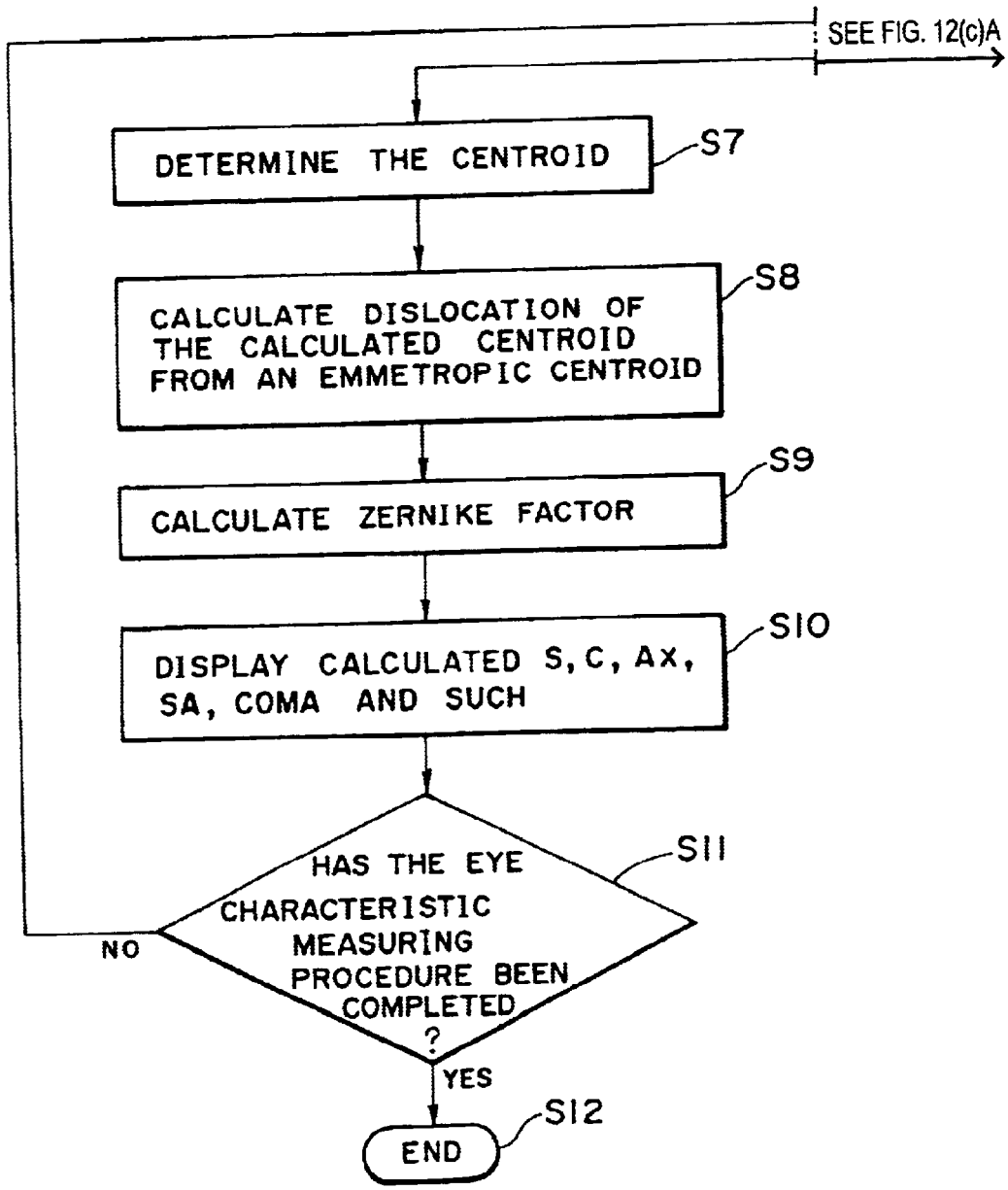
FIG. 12(c)B

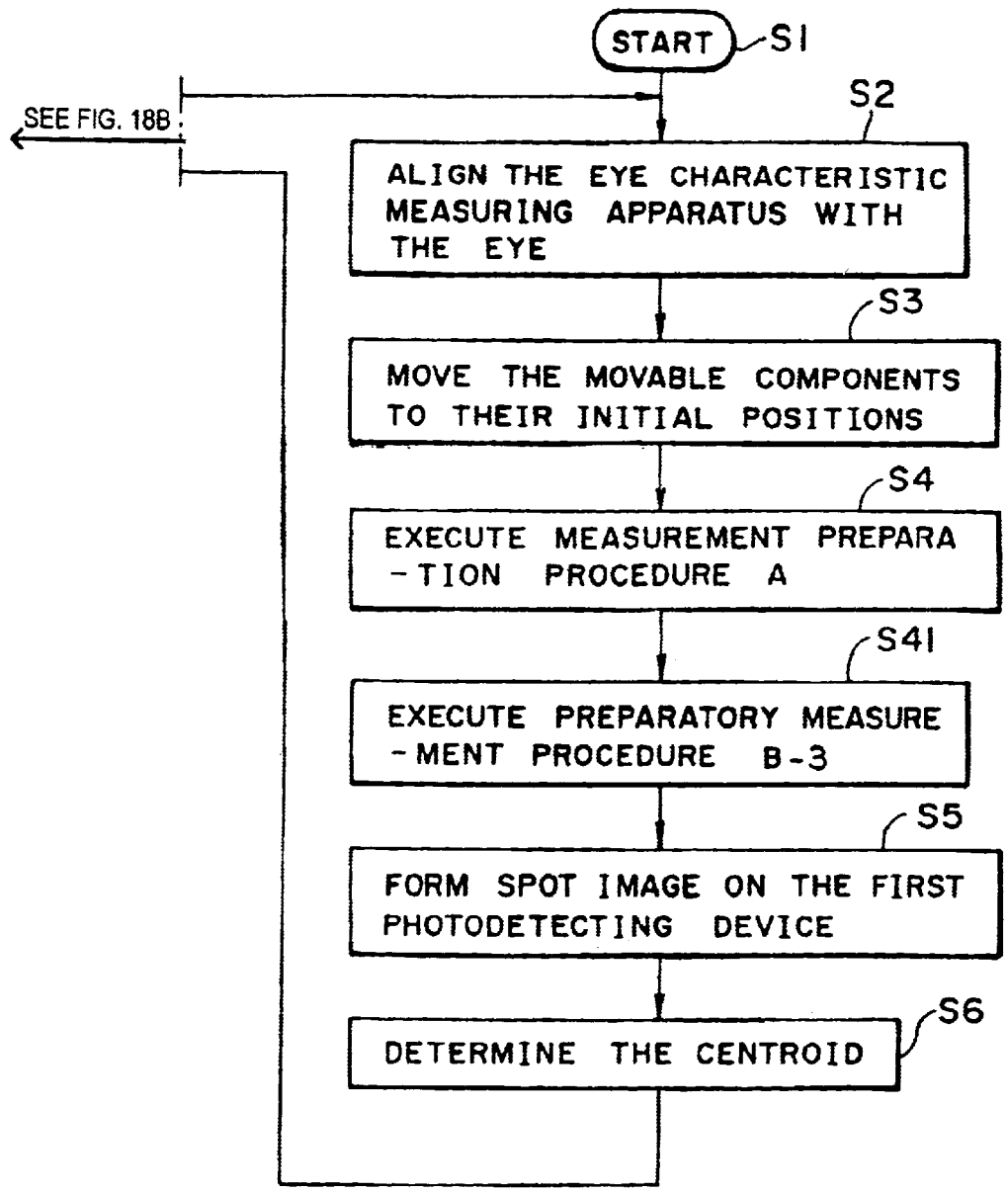
F I G. 18A

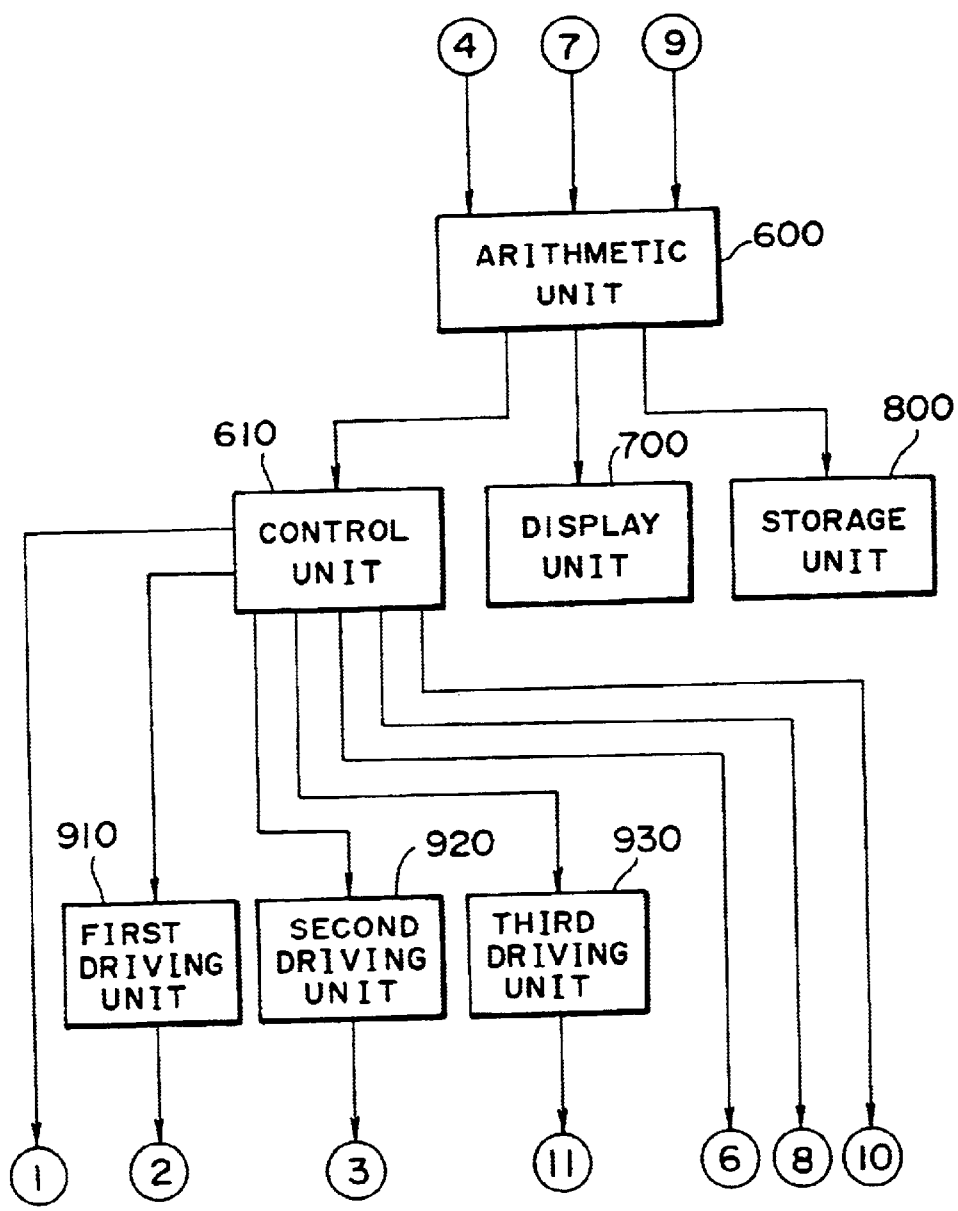
F I G. 23

EYE CHARACTERISTIC MEASURING APPARATUS

BACKGROUND OF THE INVENTION

The present invention relates an apparatus for precisely measuring eye characteristics and, more particularly, to an eye characteristic measuring apparatus provided with an image forming condition changing unit for properly adjusting illumination and capable of determining an optimum illuminating condition and an optimum light receiving condition.

A known measuring apparatus for measuring the optical characteristics of the eye focuses an illuminating optical system on the light receiving level of a first photodetecting device and focuses a photodetecting optical system on the basis of an optical characteristic (S) determined from the output of the first photodetecting device. Data provided by the known measuring apparatus for measuring the optical characteristics of the eye can be used only for correcting spectacles, and accordingly it does not have a satisfactory performance.

SUMMARY OF THE INVENTION

Accordingly, it is an object of the present invention to provide an eye characteristic measuring apparatus capable of providing sufficient data on eye characteristics of the eye.

According to the present invention, an eye characteristic measuring apparatus comprises a first light source that emits light, a first illuminating optical system capable of illuminating a small region of the retina of the eye in a variable illuminating condition, a first photodetecting optical system provided with a first transforming device that divides the reflected light beam into at least seventeen light beams and a first photodetecting device that receives part of reflected light reflected from the retina through the first transforming device, an arithmetic unit that determines the optical characteristics of the eye on the basis of a first signal provided by the first photodetecting device and corresponding to the inclination of the light, and an image forming condition changing unit that changes the respective image forming conditions of the first illuminating optical system and the first photodetecting optical system according to the level of the first signal provided by the first photodetecting device.

BRIEF DESCRIPTION OF THE DRAWINGS

The above and other objects, features and advantages of the present invention will become more apparent from the following description taken in connection with the accompanying drawings, in which:

FIG. 4 is a flow chart a measurement preparation procedure A;

FIG. 12(a) is a flow chart of a measuring procedure to be carried out by the eye characteristic measuring apparatus in the third embodiment;

FIG. 12(b) is a flow chart of a measuring procedure to be carried out by the eye characteristic measuring apparatus in the second embodiment;

FIG. 12(c) is a flow chart of a measuring procedure to be carried out by the eye characteristic measuring apparatus in the second embodiment;

FIG. 23 is a block diagram of an electrical system included in the eye characteristic measuring apparatus in the modification of the eye characteristic measuring apparatus in the fourth embodiment.

DESCRIPTION OF THE PREFERRED EMBODIMENTS

First Embodiment

Figure 1:
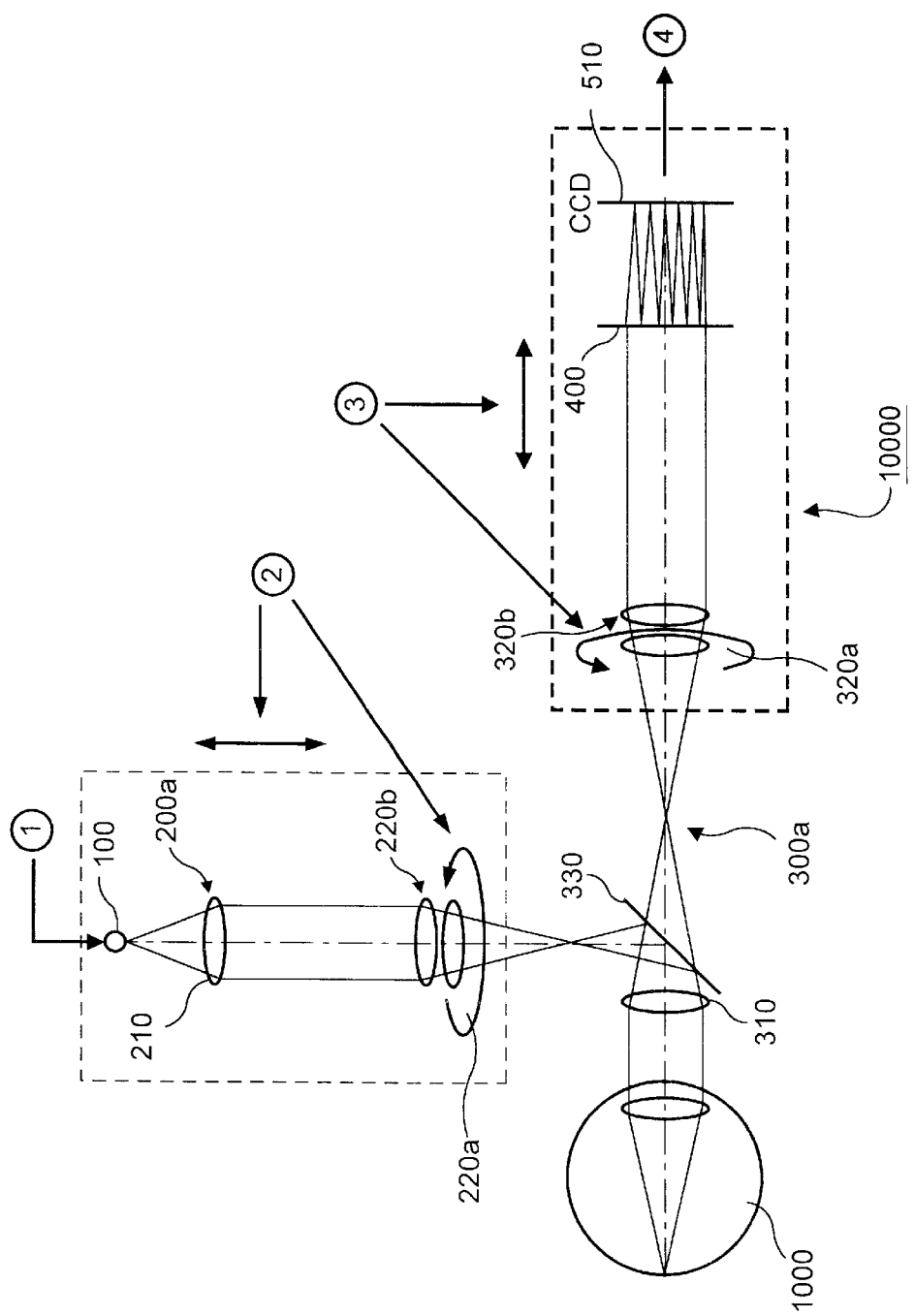
FIG. 1 is a diagrammatic view of an eye characteristic measuring apparatus in a first embodiment according to the present invention.
Figure 2:
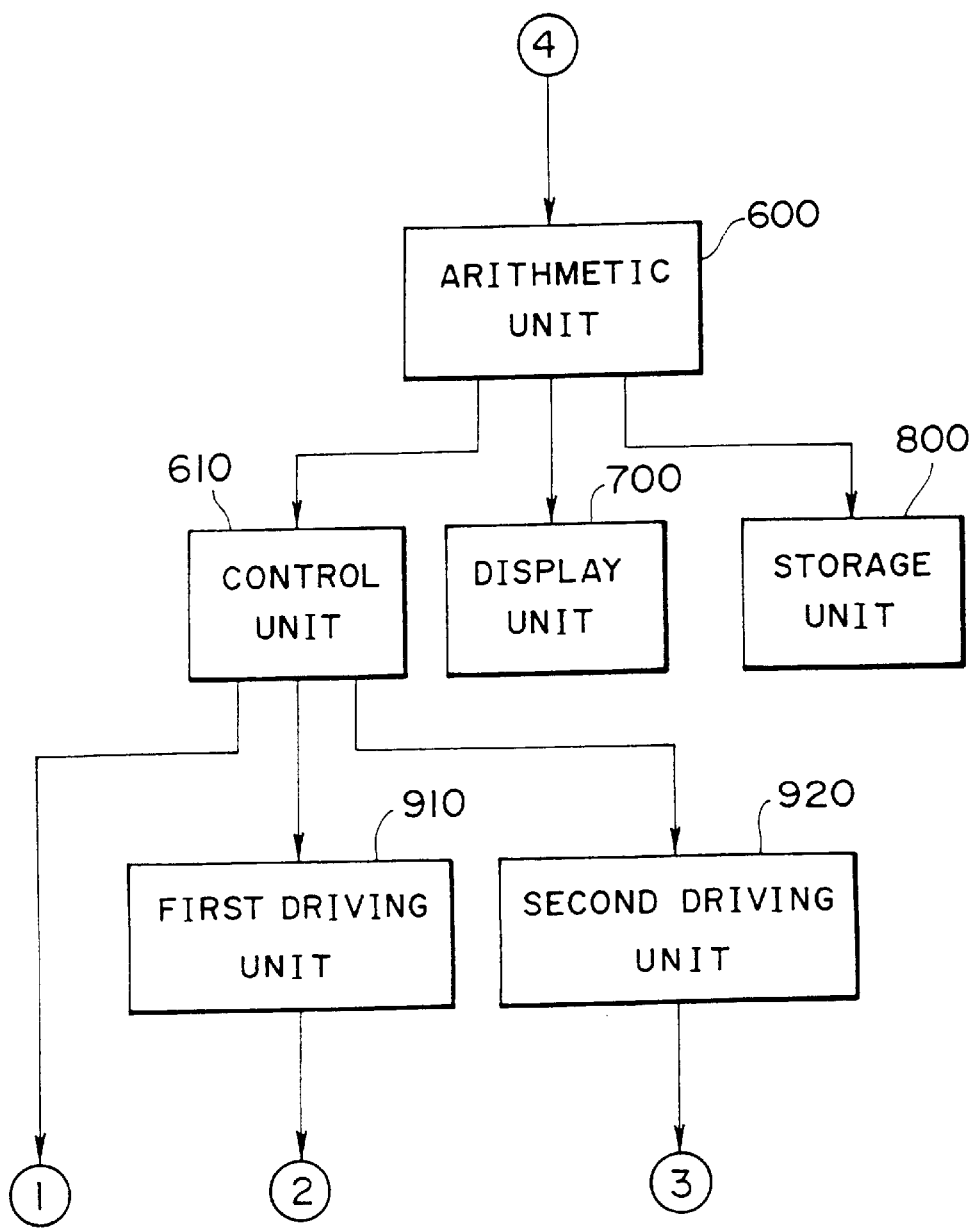
FIG. 2 is a block diagram of an electrical system included in the eye characteristic measuring apparatus in the first embodiment.

Referring to FIGS. 1 and 2, an eye characteristic measuring apparatus 10000 in a first embodiment according to the present invention includes a first light source 100 that emits light of a first wavelength, a first illuminating optical system 200A capable of illuminating a small region of the retina of the eye 1000 with light emitted by the first light source 100 in various illuminating conditions, a first photodetecting optical system 300A that guides reflected light reflected from the retina of the eye 1000 through a first transforming device 400 that divides the reflected light into at least seventeen light beams to a first photodetecting device 510, an arithmetic unit 600 that determines the optical characteristics of the eye 1000 on the basis of a first signal provided by the first photodetecting device 510 and corresponding to the inclination of the light beam, and an image forming condition changing unit that changes the respective image forming conditions of the first illuminating optical system 200A and the first photodetecting optical system 300A according to the level of the first signal provided by the first photodetecting device 510.

The arithmetic unit 600 controls all the units and systems including a control unit 610. The control unit 610 controls and drives the first light source 100 and such.

It is desirable that the first light source 100 emits light having a high spatial coherence and a low temporal coherence. The first light source 100 of the first embodiment is an SLD, a point source of a high luminance.

The first light source 100 of the first embodiment does not need necessarily to be an SLD and a laser that emits light having a high spatial coherence and a high temporal coherence may be used in combination with a rotational diffusion plate that lowers the temporal coherence properly.

An SLD that emits light having a low temporal coherence and a low spatial coherence can be used by placing a screen provided with a pinhole at a position corresponding to the light source, provided that the SLD has a sufficiently high luminous intensity.

The illuminating light emitted by the first light source 100 may be light of a wavelength in an infrared region, such as 780 nm. When the first light source 100 is kept turned on, the first photodetecting device 510 receives both light for optical characteristic measurement and light from the anterior segment of the eye 1000.

The first illuminating optical system 200A illuminates a small region of the retina of the eye 1000 with the light emitted by the first light source 100. The first illuminating optical system 200A includes a first condenser lens 210, a first cylindrical lens 220a and a relay lens 200b.

The first photodetecting optical system 300A receives the light reflected from the retina of the eye 1000 and guides the same to the first photodetecting device 510. The first photodetecting optical system 300A includes a first afocal lens 310, a second cylindrical lens 320a, a second relay lens 320b, a first beam splitter 330 and a transforming device 400 for dividing the reflected light into at least seventeen light beams.

The first beam splitter 330 of the first photodetecting optical system 300A deflects the light emitted by the first illuminating optical system 200A toward the eye 1000 and transmits the reflected light reflected from the eye 1000.

The first photodetecting device 510 receives the light through the first receiving optical system 300A and the transforming device 400 and generates a first signal.

The first light source 100 and the retina of the eye 1000 are conjugate to each other. The fundus of the eye 1000 and the first photodetecting device 510 are conjugate to each other. The transforming device 400 and the pupil of the eye 1000 are conjugate to each other.

The front focus of the first afocal lens 310 coincides substantially with the anterior segment of the eye 1000.

The first illuminating optical system 200A and the first photodetecting optical system 300A are disposed in a positional relation that makes a maximum the peak of the signal generated by the first photodetecting device 510 upon the reception of the light emitted by the first light source 100 and reflected at a point where the light is focused, are coordinated, move in directions to increase the peak of the signal generated by the first photodetecting device 510 and stop at positions where the intensity of the signal is a maximum. In such a state, the light emitted by the first light source 100 is focused on the eye 1000.

The transforming device 400 will be explained. The transforming device 400 included in the first photodetecting optical system 300A is a wavefront transforming device that coverts the reflected light into a plurality of light beams. The transforming device 400 employed in the first embodiment comprises a plurality of micro Fresnel lenses arranged in a plane perpendicular to the optical axis.

The micro Fresnel lens will be described. The micro Fresnel lens is an optical element having annular ridges arranged at a pitch for a wavelength and having a blaze angle optimum for making an outgoing light beam travel toward a point where light rays are converged. The micro Fresnel lenses are fabricated by microprocessing techniques for fabricating semiconductor devices, have eight levels of optical path differences and are capable of condensing light at a condensing efficiency of 98%.

The reflected light reflected from the fundus travels through the first afocal lens 310, the second cylindrical lens 320a and the transforming device 400 and is focused as first-order light on the first photodetecting device 510. Zero-order light is transmitted light and first-order light is condensed light.

The transforming device 400 may comprises at least seventeen converging microlens units formed in seventeen regions and a transmitting opening.

The transforming device 400 employed in the first embodiment is a wavefront transforming device capable of transforming the reflected light into at least seventeen light beams.

The first photodetecting device 510 receives the plurality of light beams provided by the transforming device 400. In the first embodiment, the first photodetecting device 510 is a CCD that does not generate much read-out noise. The CCD may be of any type, such as a general low-noise CCD or a cooled CCD for measurement provided with 2000×2000 elements.

An image signal provided by a low-noise CCD and a driver for driving the CCD can be simply achieved by using a corresponding image input board.

An electrical system included in the eye characteristic measuring apparatus 10000 will be described with reference to FIG. 2. The electrical system includes an arithmetic unit 600, a control unit 610, a display unit 700, a storage unit 800, a first driving unit 910 and a second driving unit 920.

The control unit 610 controls the first light source 100, the first driving unit 910 and the second driving unit 920 according to control signals given thereto by the arithmetic unit 600.

The first driving unit 910 drives the first cylindrical lens 220a of the first illuminating optical system 200A according to a signal given to the arithmetic unit 600 by the first photodetecting device 510. The first driving unit 910 drives a lens moving mechanism to turn the first cylindrical lens 220a.

The second driving unit 920 drives the second cylindrical lens 320a of the photodetecting optical system 300A according to a signal given to the arithmetic unit 600 by the first photodetecting device 510. The second driving unit 920 drives a lens moving mechanism to turn the second cylindrical lens 320a.

The construction of the first cylindrical lens 220a and the second cylindrical lens 320a and a method of driving the cylindrical lenses 220a and 320a will be described hereinafter. Each of the cylindrical lenses 220a and 320a have a pair of cylindrical lenses.

Suppose that cylinders have cylindrical powers D and –D, the cylinders are placed in a coordinate system defined by an x-axis and a y-axis perpendicular to the x-axis, and the respective axes of the cylinders having the cylindrical powers. D and –D are inclined to the x-axis at $\phi_+$ and $\phi v$. Then, astigmatisms at an angle $\theta$ is:

$$D \cdot \cos 2(\theta - \phi_+)$$

$$-D \cdot \cos 2(\theta - \phi_-)$$

Therefore, composite astigmatism As ($\theta$) is expressed by:

$$\begin{aligned} As(\theta) &= D \cdot \cos 2(\theta - \phi_+) + D \cdot \cos 2(\theta - \phi_-) \\ &= D\{\cos 2(\theta - \phi_+) + \cos 2(\theta - \phi_-)\} \\ &= D[-2\sin\{2(2\theta - \phi_+ - \phi_-)/2\}\sin\{2(-\phi_+ + \phi_-)/2\}] \\ &= -2D\{\sin(2\theta - \phi_+ - \phi_-)\sin(-\phi_+ + \phi_-)\} \end{aligned}$$

The maximum composite astigmatism is the composite cylindrical power.

$$\sin(2\theta - \phi_+ - \phi_-) = 1$$

Therefore, when $\theta = \{(\phi_+ - \phi_-)/2\} + 45°$ ($\theta$ is an angle defining the direction of cylindrical power), $$As\,(\theta) = 2D \sin \alpha$$

where a maximum value of $[\alpha = \phi_+ - \phi_-$. (The cross angle (Opening angle))] is applied and the cylindrical power C is provided.

The first driving unit 910, the second driving unit 920 and the lens moving mechanisms correspond to the image forming condition changing unit that changes the respective image forming conditions of the first illuminating optical system 200A and the first photodetecting optical system 300A.

An eye characteristic measuring procedure to be carried out by the eye characteristic measuring apparatus 10000 will be described with reference to FIG. 3. The eye characteristic measuring procedure is started in step S1. The alignment of the eye characteristic measuring apparatus with the eye is adjusted in step S2. In step S3, the control unit 610 controls the first driving unit 910 and the second driving unit 920 according to control signals provided by the arithmetic unit 600 to set the movable units at their initial positions; that is the first driving unit 910 moves the first illuminating optical system 200A to its initial position by driving a lens moving mechanism, and the second driving unit 920 moves the photodetecting optical system 300A to its initial position by driving a lens moving mechanism. A measurement preparation procedure A is executed in step S4.

The measurement preparation procedure A will be described with reference to FIG. 4. The measurement preparation procedure A is started in step S1. The first photodetecting device 510 measures a spot image level $L_s$ in step S2. The arithmetic unit 600 decides whether the spot image level $L_s$ is higher than a predetermined level $L_0$ in step S3. If the spot image level $L_s$ is higher than the predetermined level $L_0$, the procedure proceeds to step S4 to end the measuring preparation procedure.

Although the measurement preparation procedure A makes a decision on the basis of the spot image level $L_s$ in the first embodiment, when the arithmetic unit 600 decides that the distribution of spots of the beams transformed by the transforming device 400 on the first photodetecting device 510 is excessively dense, the image forming conditions of the first illuminating optical system 200A and the first photodetecting optical system 300A may be changed so that the spots of the light beams are distributed properly on the first photodetecting device 510 by a preparatory measurement procedure B, which will be described later in connection with a second modification of a second embodiment.

If it is decided in step S3 that the spot image level $L_s$ is not higher than the predetermined level $L_0$, the image forming condition changing unit is controlled to correct illuminating conditions and light receiving conditions in step S5. The arithmetic unit 600 controls the first driving unit 910 to move the illuminating optical system 200A for correcting illuminating conditions. The arithmetic unit 600 controls the second driving unit 920 to move the photodetecting optical system 300A to correct light receiving conditions. After the completion of the correction of the illuminating conditions and light receiving conditions in step S5, the procedure returns to step S2.

Referring again to FIG. 3, after the completion of step S4, a spot image is formed on the first photodetecting device 510 in step S5. The centroid of the spot image is determined in step S6. The centroid can be determined, for example, by projecting light on a plurality of pixels on the light receiving surface and measuring light intensities on the pixels. Thus, the position of the centroid can be measured in an accuracy not greater than 1/10 of the element.

In step S7, dislocation of the measured centroid from an emmetropic centroid is calculated.

In step S8, Zernike factor is calculated by using Expressions (1) to (6), which will be described later.

In step S9, the calculated spherical power, cylindrical power, angle of astigmatic axis, spherical aberration, coma and other high-order aberration components (S, C, Ax, SA, Coma and such) of the eye are displayed on the screen of the display unit 700.

A query is made in step S10 to see whether the eye characteristic measuring procedure has been completed. If the eye characteristic measuring procedure has been completed, the eye characteristic measuring procedure is ended in step S11. If the eye characteristic measuring procedure has not yet been completed, the eye characteristic measuring procedure returns to step S2.

The changeable illuminating conditions of the first illuminating optical system 200A are those concerned with the focused state of the illuminating light for illuminating the fundus. The image forming conditions that can be changed by the image forming condition changing unit may be those concerned with the condensed state of the light received by the first photodetecting device 510.

First Modification of the First Embodiment

A first modification of the eye characteristic measuring apparatus in the first embodiment will be described.

The image forming condition changing unit of the first embodiment changes the image forming conditions of the first illuminating optical system 200A and the first photodetecting optical system 300A according to the level of the first signal provided by the first photodetecting device 510. An image forming condition changing unit included in the first modification of the first embodiment changes the image forming conditions of the first illuminating optical system 200A and the first photodetecting optical system 300A according to optical characteristics determined by the arithmetic unit 600.

Figure 5:
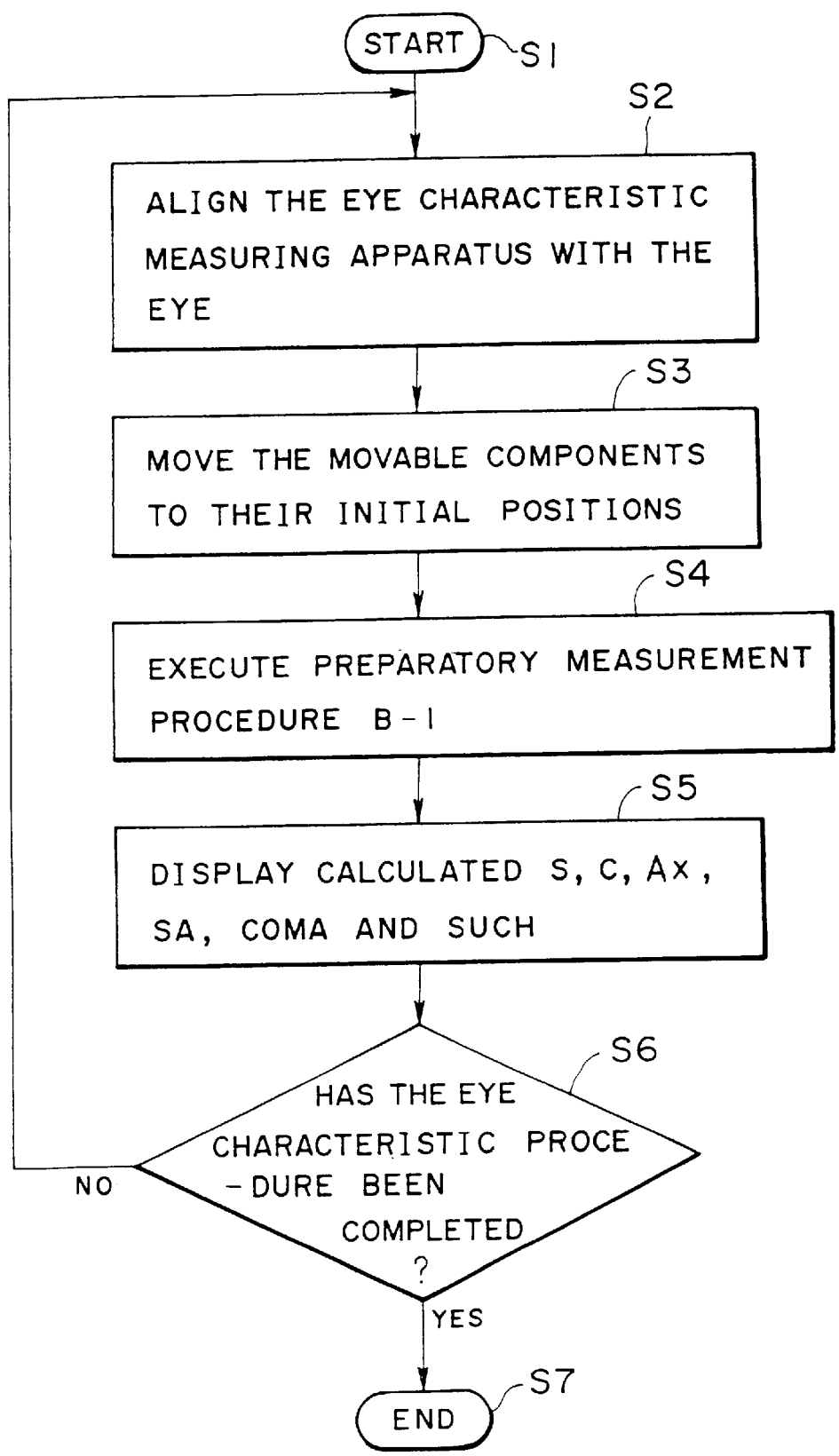
FIG. 5 is a flow chart of an eye characteristic measuring procedure to be carried out by an eye characteristic measuring apparatus in a first modification of the eye characteristic measuring apparatus in the first embodiment.

An eye characteristic measuring procedure to be carried out by the first modification of the eye characteristic measuring apparatus 10000 will be described with reference to FIG. 5. The eye characteristic measuring procedure is started in step S1. The alignment of the eye characteristic measuring apparatus with the eye is adjusted in step S2. In step S3, the control unit 610 controls the first driving unit 910 and the second driving unit 920 according to control signals provided by the arithmetic unit 600 to set the movable units at their initial positions; that is the first driving unit 910 moves the first illuminating optical system 200A to its initial position by driving a lens moving mechanism, and the second driving unit 920 moves the photodetecting optical system 300A to its initial position by driving a lens moving mechanism.

A preparatory measurement procedure B-1 is executed in step S4.

Figure 6:
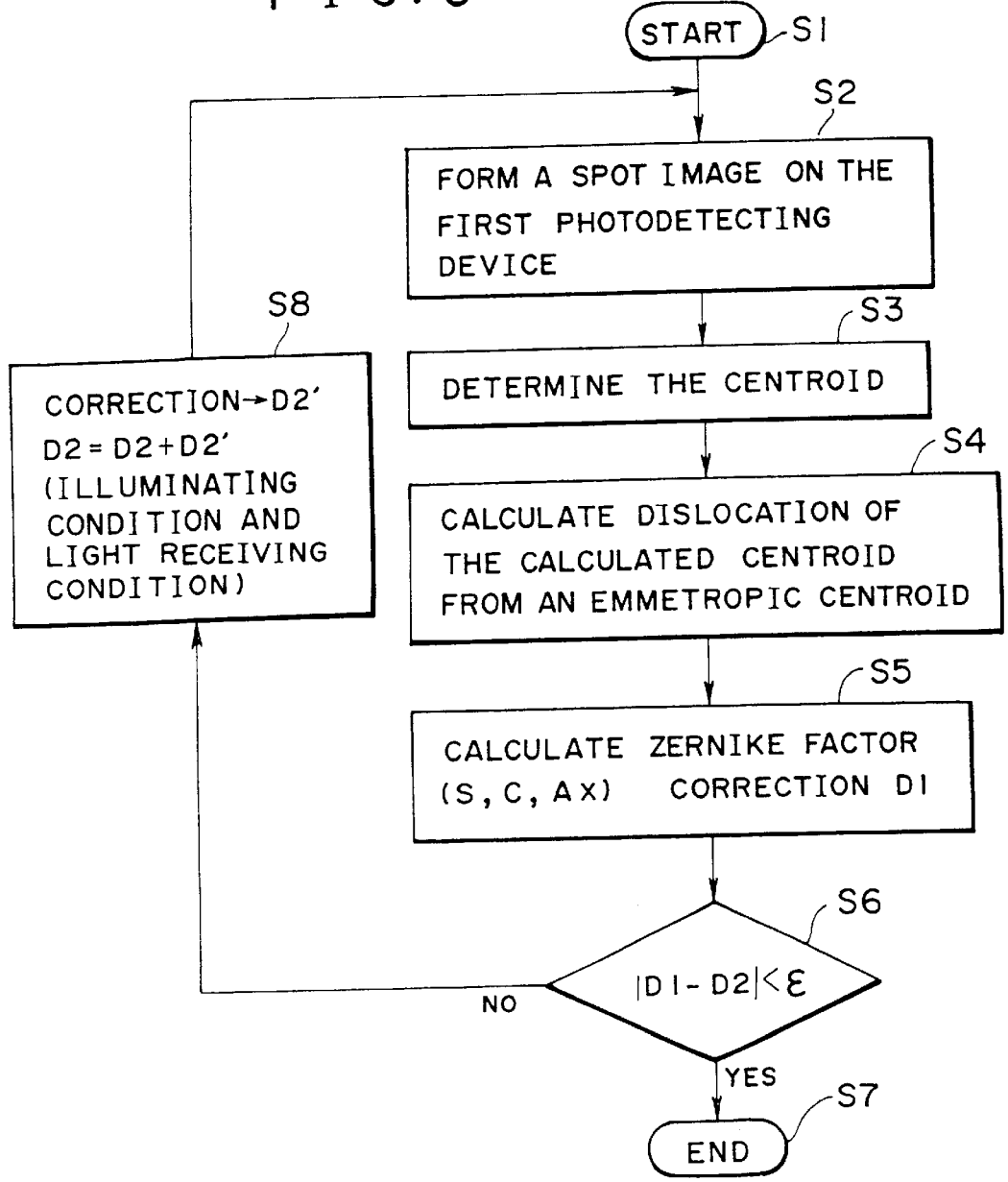
FIG. 6 is a flow chart of a preparatory measurement procedure B-1.

The preparatory measurement procedure B-1 will be described with reference to FIG. 6. The preparatory measurement procedure B-1 is started in step S1. A spot image is formed on the first photodetecting device 510 in step S2. The centroid of the spot image is determined, for example, on the basis of the respective intensities of light rays falling on a plurality of pixels on the light receiving surface. Thus, the position of the centroid can be calculated in an accuracy not greater than 1/10 of the element.

The dislocation of the calculated centroid from an emmetropic centroid is calculated in step S4.

In step S5, Zernike factor is calculated by using Expressions (1) to (6), which will be described later.

A correction D1 is calculated on the basis of the values of spherical power, cylindrical power and angle of astigmatic axis (S, C, Ax) calculated in step S5.

In step S6, a query is made to see if a correction D2 meets an inequality:

$$|D2-D1|<\epsilon$$

and when D2 meets the inequality, the preparatory measurement procedure B-1 is ended in step S7.

If the correction D2 does not meet the inequality, a correction D2' is added to the correction D2, and the image forming condition changing unit is controlled to correct illuminating conditions and light receiving conditions in step S8; that is the arithmetic unit 600 controls the first driving unit 910 to change illuminating conditions by moving the first illuminating optical system 200A for correction. The arithmetic unit 600 controls the second driving unit 920 to change light receiving conditions for correction by moving the photodetecting optical system 300A. After executing step S6, the procedure returns to step s2.

Referring again to FIG. 5, after the completion of the preparatory measurement procedure B-1 in step S4, the calculated spherical power, cylindrical power, angle of astigmatic axis, spherical aberration, coma and other high-order aberration components (S, C, Ax, SA, Coma and such) of the eye are displayed on the screen of the display unit 700 in step S5.

A query is made in step S6 to see whether the eye characteristic measuring procedure has been completed. If the eye characteristic measuring procedure has been completed, the eye characteristic measuring procedure is ended in step S7. If the eye characteristic measuring procedure has not yet been completed, the eye characteristic measuring procedure returns to step S2.

Second Modification of the First Embodiment

A second modification of eye characteristic measuring apparatus in the first embodiment will be described.

The image forming condition changing unit of the first embodiment changes the image forming conditions of the first illuminating optical system 200A and the first photodetecting optical system 300A according to the level of the first signal provided by the first photodetecting device 510. An image forming condition changing unit included in the second modification of the first embodiment changes the image forming conditions of the first illuminating optical system 200A and the first photodetecting optical system 300A according to the level of the first signal provided by the first photodetecting device 510 to set the first illuminating optical system 200A and the first photodetecting optical system 300A in a first changed state, and then changes the image forming conditions of the first illuminating optical system 200A and the first photodetecting optical system 300A according to optical characteristics determined by the arithmetic unit 600 to set the first illuminating optical system 200A and the first photodetecting optical system 300A in a second changed state.

Figure 7:
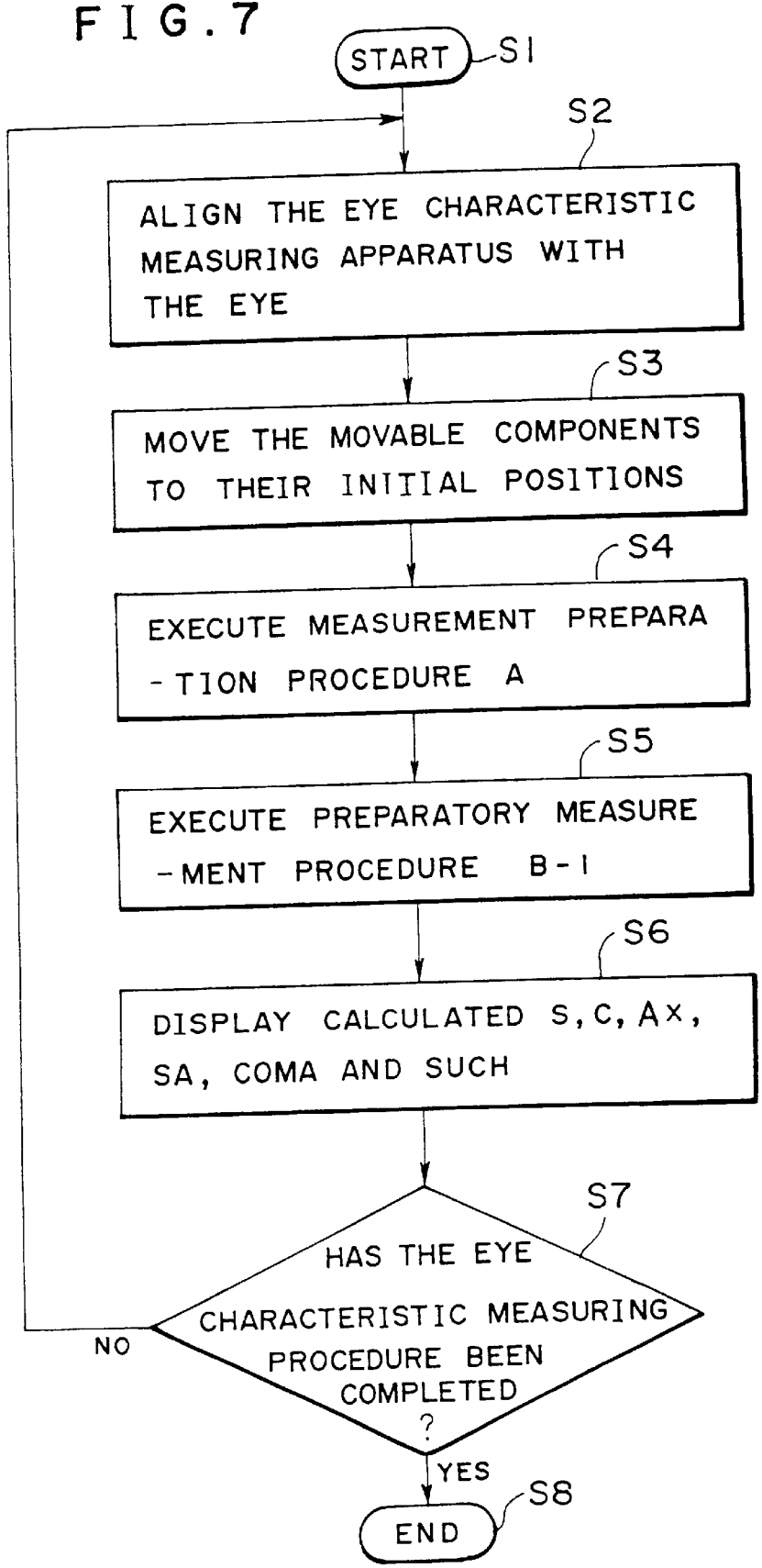
FIG. 7 is a is a flow chart of an eye characteristic measuring procedure to be carried out by an eye characteristic measuring apparatus in a second modification of the eye characteristic measuring apparatus in the first embodiment.

An eye characteristic measuring procedure to be carried out by the second modification of the eye characteristic measuring apparatus 10000 will be described with reference to FIG. 7. The eye characteristic measuring procedure is started in step S1. The alignment of the eye characteristic measuring apparatus with the eye is adjusted in step S2. In step S3, the control unit 610 controls the first driving unit 910 and the second driving unit 920 according to control signals provided by the arithmetic unit 600 to set the movable units at their initial positions; that is the first driving unit 910 moves the first illuminating optical system 200A to its initial position by driving a lens moving mechanism, and the second driving unit 920 moves the photodetecting optical system 300A to its initial position by driving a lens moving mechanism.

The measurement preparation procedure A is carried out in step S4. The measurement preparation procedure A is the same as that shown in FIG. 4 and hence the description thereof will be omitted.

After the completion of the measurement preparation procedure A in step S4, the preparatory measurement procedure B-1 is carried out in step S5. The preparatory measurement procedure B-1 is the same as that shown in FIG. 6 and hence the description thereof will be omitted.

After the completion of the preparatory measurement procedure B-1 in step S5, the calculated spherical power, cylindrical power, angle of astigmatic axis, spherical aberration, coma and other high-order aberration components (S, C, Ax, SA, Coma and such) of the eye are displayed on the screen of the display unit 700 in step S6.

A query is made in step S7 to see whether measurement has been completed. The eye characteristic measuring procedure is ended in step S8 if the response in step S7 is affirmative. The procedure returns to step S2 if the response in step S7 is negative.

Second Embodiment

Figure 8:
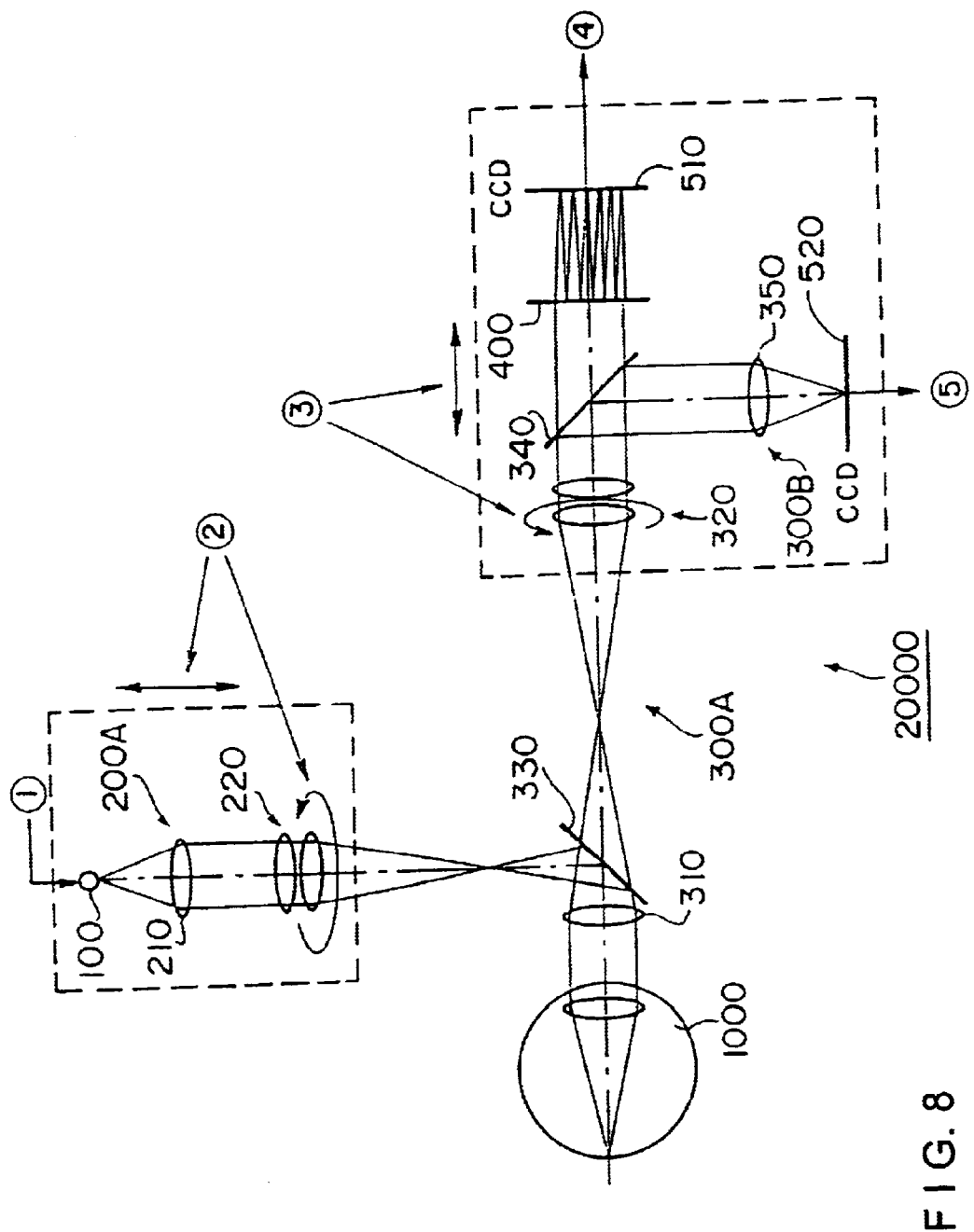
FIG. 8 is a diagrammatic view of an eye characteristic measuring apparatus in a second embodiment according to the present invention.
Figure 9:
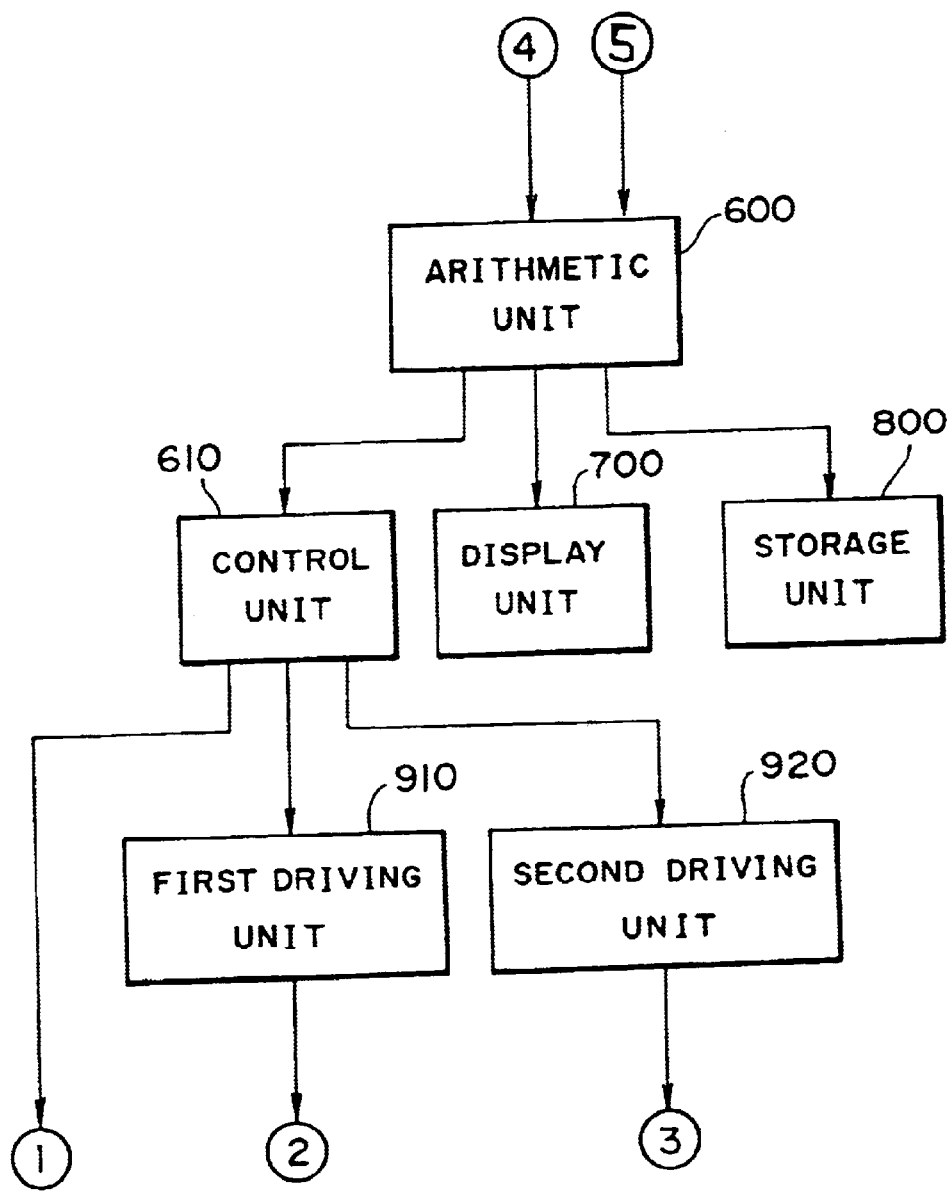
FIG. 9 is a block diagram of an electrical system included in the eye characteristic measuring apparatus in the second embodiment.

Referring to FIGS. 8 and 9, an eye characteristic measuring apparatus 20000 in a second embodiment according to the present invention includes a first light source 100 that emits light of a first wavelength, a first illuminating optical system 200A capable of illuminating a small region of the retina of the eye 1000 with light emitted by the first light source 100 in various illuminating conditions, a first photodetecting optical system 300A that guides reflected light reflected from the retina of the eye 1000 through a first transforming device 400 that divides the reflected light into at least seventeen light beams to a first photodetecting device 510, a second photodetecting optical system 300B that guides reflected light reflected from the retina of the eye 1000 to a second photodetecting device 520, an arithmetic unit 600 that determines the optical characteristics of the eye 1000 on the basis of a first signal provided by the first photodetecting device 510 and corresponding to the inclination of the light, and an image forming condition changing unit that changes the respective image forming conditions of the first illuminating optical system 200A and the first photodetecting optical system 300A according to the level of a second signal provided by the second photodetecting device 520.

The arithmetic unit 600 determines the optical characteristics of the eye 1000 on the basis of the first signal provided by the first photodetecting device 510 and corresponding to the inclination of light.

The image forming condition changing unit changes the image forming conditions for the first illuminating optical system 200A and the first photodetecting optical system 300A according to the level of the second signal provided by the second photodetecting device 520.

The first photodetecting optical system 300A includes a first afocal lens 310, a second cylindrical lens 320a, a second relay lens 320b, a first beam splitter 330, a second beam splitter 340, and a transforming device 400 that divides the reflected light into at least seventeen light beams.

The first photodetecting device 510 receives light traveling through the first photodetecting optical system 300A and the transforming device 400 and generates a first signal.

The second photodetecting optical system 300B includes the first afocal lens 310, the second cylindrical lens 320a, the second relay lens 320b, the first beam splitter 330, the second beam splitter 340 and a second condenser lens 350. Light reflected by the second splitter 340 disposed between the second cylindrical lens 320 and the transforming device 400 travels through the second condenser lens 350 and falls on a second photodetecting device 520. The second photodetecting device 520 generates a second signal.

The first light source 100 and the fundus of the eye 100 are conjugate to each other. The fundus of the eye 100 and the first and the second photodetecting device 510 and 520 are conjugate to each other. The transforming device 400 and the pupil of the eye 1000 are conjugate to each other.

The eye characteristic measuring apparatus in the second embodiment is the same in other respects as that in the first embodiment and hence further description thereof will be omitted.

An electrical system included in the eye characteristic measuring apparatus 20000 will be described with reference to FIG. 9. The electrical system includes an arithmetic unit 600, a control unit 610, a display unit 700, a storage unit 800, a first driving unit 910 and a second driving unit 920.

The arithmetic unit 600 receives the first signal from the first photodetecting device 510 and the second signal from the second photodetecting device 520. The arithmetic unit 600 determines the optical characteristics of the eye 1000 on the basis of the second signal provided by the second photodetecting device 520, controls the image forming condition changing unit to change the image forming conditions of the first illuminating optical system 200A and the first photodetecting optical system 300A.

An eye characteristic measuring procedure to be carried out by the eye characteristic measuring apparatus 20000 will be described with reference to FIG. 3. The eye characteristic measuring procedure is started in step S1. The alignment of the eye characteristic measuring apparatus with the eye is adjusted in step S2. In step S3, the control unit 610 controls the first driving unit 910 and the second driving unit 920 according to control signals provided by the arithmetic unit 600 to set the movable units at their initial positions; that is the first driving unit 910 moves the first illuminating optical system 200A to its initial position by driving a lens moving mechanism, and the second driving unit 920 moves the second cylindrical lens 320 of the photodetecting optical system 300A to its initial position by driving a lens moving mechanism.

A measurement preparation procedure A is executed in step S4. The measurement preparation procedure A uses the second photodetecting device 520 as shown in FIG. 10. The measurement preparation procedure A will be described with reference to FIG. 10.

The measurement preparation procedure A is started in step S1. The second photodetecting device 520 measures a spot image level $L_s$ in step S2. The arithmetic unit 600 decides whether the spot image level $L_s$ is higher than a predetermined level $L_0$ in step S3. If the spot image level $L_s$ is higher than the predetermined level $L_0$, the procedure proceeds to step S4 to end the measuring preparation procedure.

If it is decided in step S3 that the spot image level $L_s$ is not higher than the predetermined level $L_0$, the image forming condition changing unit is controlled to correct illuminating conditions and light receiving conditions in step s5. The arithmetic unit 600 controls the first driving unit 910 to move the illuminating optical system 200A for correcting illuminating conditions. The arithmetic unit 600 controls the second driving unit 920 to move the photodetecting optical system 300A to correct light receiving conditions. After the completion of the correction of the illuminating conditions and light receiving conditions in step S5, the procedure returns to step S2.

Referring again to FIG. 3, after the completion of step S4, a spot image is formed on the first photodetecting device 510 in step S5. The centroid of the spot image is determined in step S6. The centroid can be determined, for example, by projecting light on a plurality of pixels on the light receiving surface and measuring light intensities on the pixels. Thus, the position of the centroid can be measured in an accuracy not greater than 1/10 of the element.

In step S7, dislocation of the measured centroid from an emmetropic centroid is calculated.

In step S8, Zernike factor is calculated by using Expressions (1) to (6). In step S9, the calculated spherical power, cylindrical power, angle of astigmatic axis, spherical aberration, coma and other high-order aberration components (S, C, Ax, SA, Coma and such) of the eye are displayed on the screen of the display unit 700.

A query is made in step S10 to see whether the eye characteristic measuring procedure has been completed. If the eye characteristic measuring procedure has been completed, the eye characteristic measuring procedure is ended in step 511. If the eye characteristic measuring procedure has not yet been completed, the eye characteristic measuring procedure returns to step S2.

First Modification of the Second Embodiment

A first modification of the eye characteristic measuring apparatus in the second embodiment will be described.

The image forming condition changing unit of the second embodiment changes the image forming conditions of the first illuminating optical system 200A and the first photodetecting optical system 300A according to the level of the second signal provided by the second photodetecting device 520. An image forming condition changing unit included in the first modification of the second embodiment changes the image forming conditions of the first illuminating optical system 200A and the first photodetecting optical system 300A according to the level of the second signal provided by the second photodetecting device 520 to set a first state, and sets a second state by changing the image forming conditions of the first illuminating optical system 200A and the first photodetecting optical system 300A according to optical characteristics determined by the arithmetic unit 600.

In the first state, the image forming conditions of the first illuminating optical system 200A and the first photodetecting optical system 300A makes the level of the second signal a maximum. In the second state, the image forming conditions of the first illuminating optical system 200A and the first photodetecting optical system 300A are determined according to the optical characteristics of the eye including a spherical component, an astigmatic component and an axis of astigmatic axis so that those optical characteristics are cancelled out. More concretely, the spherical component is corrected approximately in the first state, and the spherical component is corrected precisely, the astigmatic component and the angle of astigmatic axis are corrected in the second state.

An eye characteristic measuring procedure to be carried out by the first modification of the eye characteristic measuring apparatus 20000 will be described with reference to FIG. 12(*a*).

The eye characteristic measuring procedure is started in step S1. The alignment of the eye characteristic measuring apparatus with the eye is adjusted in step S2. In step S3, the control unit 610 controls the first driving unit 910 and the second driving unit 920 according to control signals provided by the arithmetic unit 600 to set the movable units at their initial positions; that is the first driving unit 910 and the second driving unit 920 are controlled so as to move the movable units its initial position, and the second driving unit 920 moves the photodetecting optical system 300A to its initial position by driving a lens moving mechanism.

A measurement preparation procedure A is carried out in step S4. The measurement preparation procedure A is the same as that shown in FIG. 10 and described in connection with the second embodiment. The first state is set at the completion of the measurement preparation procedure A.

After the measurement preparation procedure A has been completed in step S4, a preparatory measurement procedure B-1 is executed in step S5. The preparatory measurement procedure B-1 is the same as that described in connection with the first modification of the first embodiment with reference to FIG. 6. Corrections are determined on the basis of a spherical power, a cylindrical power and an angle of astigmatic axis (S, C, Ax) and photodetecting conditions are changed on the basis of the corrections for correction.

After the completion of the preparatory measurement procedure B-1 in step S5, a spot image is formed on the first photodetecting device 510 in step S6 (FIG. 12(*b*)). Steps S6 to S10 are executed to measure the spherical power, cylindrical power, angle of astigmatic axis, spherical aberration, coma and other high-order aberration components (S, C, Ax, SA, Coma and such) of the eye and the measured data are displayed. Those steps are the same as those executed by the second embodiment and hence the further description thereof will be omitted. A query is made in step S11 to see whether the eye characteristic measuring procedure has been completed. If the eye characteristic measuring procedure has been completed, the eye characteristic measuring procedure is ended in step S12. If the eye characteristic measuring procedure has not yet been completed, the eye characteristic measuring procedure returns to step S2 and measurement is continued.

Second Modification of the Second Embodiment

The image forming condition changing unit of the second embodiment changes the image forming conditions of the first illuminating optical system 200A and the first photodetecting optical system 300A according to the level of the second signal provided by the second photodetecting device 520. An image forming condition changing unit included in the second modification of the second embodiment changes the image forming conditions of the first illuminating optical system 200A and the first photodetecting optical system 300A according to the level of the second signal provided by the second photodetecting device 520 to set a first state, and sets a second state by changing the image forming conditions of the first illuminating optical system 200A and the first photodetecting optical system 300A according to a signal provided by the first photodetecting device 510.

In the first state, the image forming conditions of the first illuminating optical system 200A and the first photodetecting optical system 300A makes the level of the second signal a maximum. In the second state, the image forming conditions of the first illuminating optical system 200A and the first photodetecting optical system 300A are determined according to the level of a signal provided by the first photodetecting device 510 or the position of a light spot on the first photodetecting device 510. More concretely, the spherical component is corrected approximately in the first state, and the spherical component is corrected precisely, the astigmatic component and the angle of astigmatic axis are corrected in the second state.

An eye characteristic measuring procedure to be carried out by the second modification, of the eye characteristic measuring apparatus 20000 will be described with reference to FIG. 12(*c*).

The eye characteristic measuring procedure is started in step S1. The alignment of the eye characteristic measuring apparatus with the eye is adjusted in step S2. In step S3, the control unit 610 controls the first driving unit 910 and the second driving unit 920 according to control signals provided by the arithmetic unit 600 to set the movable units at their initial positions; that is the first driving unit 910 and the second driving unit 920 are controlled so as to move the movable units to their initial positions. The second driving unit 920 moves the photodetecting optical system 300A to its initial position by driving a lens moving mechanism.

A measurement preparation procedure A is carried out in step S4. The measurement preparation procedure A is the same as that shown in FIG. 10 and described in connection with the second embodiment. The first state is set at the completion of the measurement preparation procedure A. After the measurement preparation procedure A has been completed in step S4, a preparatory measurement procedure B is executed in step S5. The preparatory measurement procedure B changes the image forming conditions of the first illuminating optical system 200A and the first photodetecting optical system 300A according to a signal provided by the first photodetecting device 510. More concretely, when the arithmetic unit 600 decides that the distribution of spots of the beams formed by the transforming device 400 in an objective region of the light receiving surface of the first photodetecting device 510 is excessively dense.due to the abnormal refraction of the eye, the image forming conditions of the first illuminating optical system 200A and the first photodetecting optical system 300A are changed so that the spots of the beams are distributed properly. For example, when the light is convergent, the image forming conditions are changed so that the degree of convergence of light is decreased.

After the preparatory measurement procedure B has been completed in step S5, a spot image is formed on the first photodetecting device 510 in step S6 (FIG. 12(c)). Steps S6 to S10 are executed to measure the spherical power, cylindrical power, angle of astigmatic axis, spherical aberration, coma and other high-order aberration components (S, C, Ax, SA, Coma and such) of the eye to be displayed. Those steps S6 to S10 are the same as those executed by the second embodiment and hence the further description thereof will be omitted. A query is made in step S11 to see whether the eye characteristic measuring procedure has been completed. If the eye characteristic measuring procedure has been completed, the eye characteristic measuring procedure is ended in step S12. If the eye characteristic measuring procedure has not yet been completed, the eye characteristic measuring procedure returns to step S2.

Third Embodiment

Figure 11:
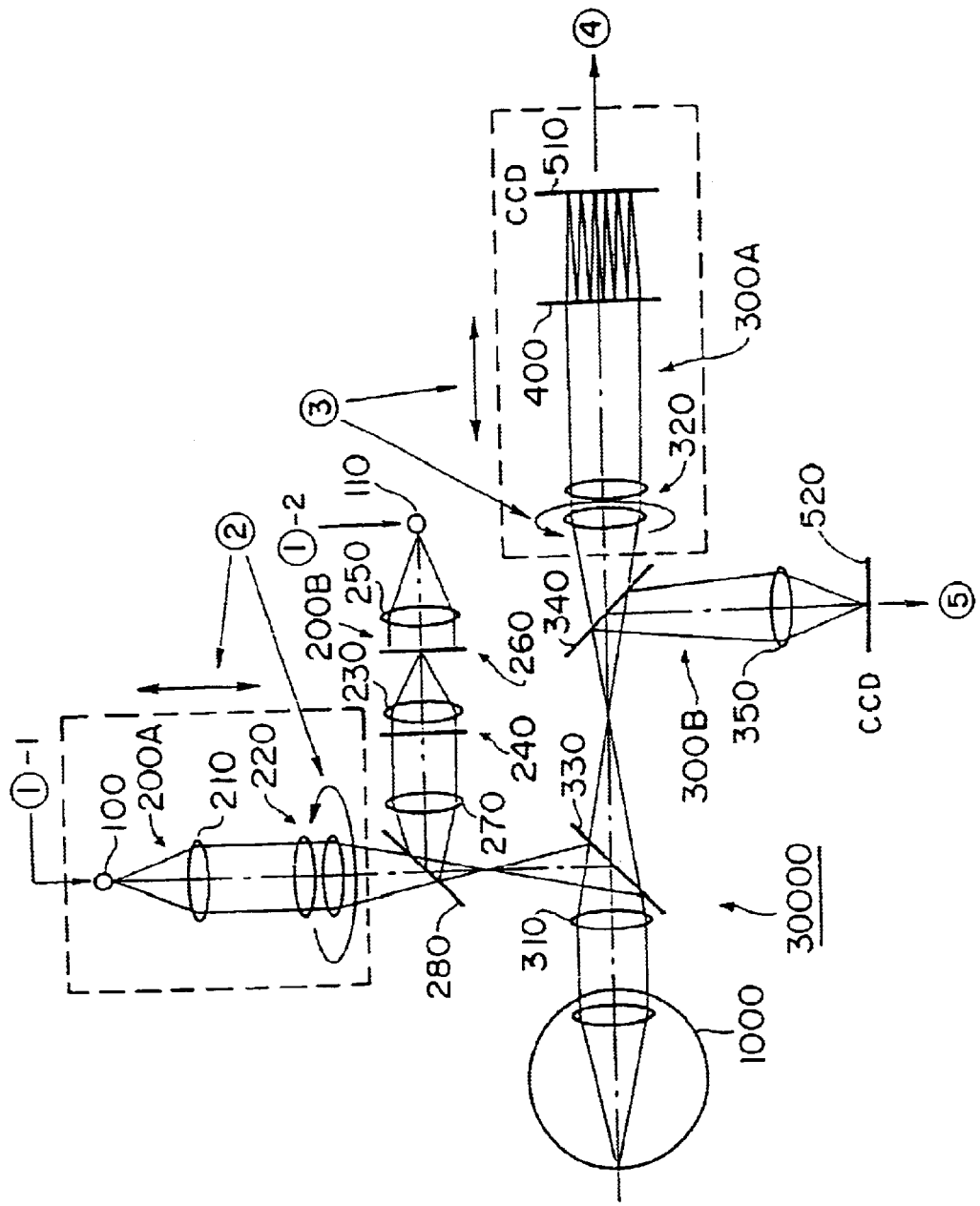
FIG. 11 is a diagrammatic view of an eye characteristic measuring apparatus in a third embodiment according to the present invention.

Referring to FIG. 11, an eye characteristic measuring apparatus 30000 in a third embodiment according to the present invention includes a first light source 100 that emits light of a first wavelength, a first illuminating optical system 200A capable of illuminating a small region of the retina of the eye 1000 with light emitted by the first light source 100, a second light source that emits light of a second wavelength, a second illuminating optical system 200B capable of illuminating a predetermined region of the retina of the eye 100 with the light of the second wavelength emitted by the second light source 110, a first photodetecting optical system 300A that guides reflected light reflected from the retina of the eye 1000 through a first transforming device 400 that divides the reflected light into at least seventeen light beams to a first photodetecting device 510, a second photodetecting optical system 300B that guides reflected light reflected from the retina of the eye 1000 to a second photodetecting device 520, an arithmetic unit 600 that determines the optical characteristics of the eye 1000 on the basis of a first signal provided by the first photodetecting device 510 and corresponding to the inclination of the light and determines the illuminating conditions of the first illuminating optical system 200A on the basis of a second signal provided by the second photodetecting device 520, and an image forming condition changing unit that changes the respective image forming conditions of the first illuminating optical system 200A and the first photodetecting optical system 300A according to the level of a first signal provided by the first photodetecting device 510 to set a first changed state and changes the image forming conditions of the first illuminating optical system 200A and the first photodetecting optical system 300A according to the optical characteristics determined by the arithmetic unit 600 to set a second changed state.

The first illuminating optical system 200A illuminates a small region of the retina of the eye 1000 with the light emitted by the first light source 100. The first illuminating optical system 200A includes a first condenser lens 210, a first cylindrical lens 220a and a first relay lens 220b.

The second illuminating optical system 200B illuminates a predetermined region of the retina of the eye with the second light emitted by the second light source 110. The second wavelength of the second light emitted by the second light source 110 is, for example, 860 nm.

The second illuminating optical system 200B includes the second light source 110, a third condenser lens 230, a first diaphragm ring 240, a fourth condenser lens 250, a second diaphragm ring 260, a lens 270 and a third beam splitter 330.

The third condenser lens 230 and the first diaphragm ring 240 are for the illumination of the pupil. The fourth condenser lens 250 and the second diaphragm ring 260 are for the illumination of the fundus.

The first photodetecting optical system 300A guides reflected light reflected from the retina of the eye and passing the second beam splitter 340 to the first photodetecting device 510. The first photodetecting optical system 300A includes a first afocal lens 310, a second cylindrical lens 320a, a second relay lens 320b, a first beam splitter 330 and a transforming device 400 that divides the reflected light into at least seventeen light beams.

The first photodetecting device 510 receives the light beams provided by the transforming device 400 of the first photodetecting optical system 300A and generates a first signal.

The second photodetecting optical system 300B includes the first afocal lens 310, the first beam splitter 330, a second beam splitter 340 and a second condenser lens 350. The light of the second wavelength reflected by the second beam splitter 340 disposed between the first beam splitter 330 and the second cylindrical lens 320 travels through the second condenser lens 350 and falls on the second photodetecting device 520. The second photodetecting device 520 generates a second signal. The second beam splitter 340 is a dichroic mirror that transmits the light of the first wave length and reflects the light of the second wavelength.

The first light source 100 and the second diaphragm ring 260 corresponding to the secondary light source of the second light source 110 are conjugate to the fundus of the eye 1000. The first photodetecting device 510 and the second photodetecting device 520 are conjugate to the fundus of the eye 1000. The transforming device 400 and the pupil are conjugate to each other. The pupil and the first diaphragm ring 240 are conjugate to each other.

The third embodiment is the same in other respects as the first and the second embodiment and hence the further description thereof will be omitted.

An electrical system included in the eye characteristic measuring apparatus 30000 will be described with reference to FIG. 9. The electrical system includes an arithmetic unit 600, a control unit 610, a display unit 700, a storage unit 800, a first driving unit 910 and a second driving unit 920.

The arithmetic unit 600 receives the first signal from the first photodetecting device 510 and a second signal from the second photodetecting device 520. The arithmetic unit 600 determines the optical characteristics of the eye 1000 on the basis of the first signal provided by the first photodetecting device 510 and determines the illuminating condition of the first illuminating optical system 200A on the basis of the second signal provided by the second photodetecting device 520.

An image forming condition changing unit included in the third embodiment changes the image forming conditions of the first illuminating optical system 200A and the first photodetecting optical system 300A according to the level of the second signal provided by the second photodetecting device 520 to set a first changed state, and sets a second changed state by changing the image forming conditions of the first illuminating optical system 200A and the first photodetecting optical system 300A according to optical characteristics determined by the arithmetic unit 600.

Although the first wavelength is shorter than the second wavelength in the third embodiment, the second wavelength may be shorter than the first wavelength. The first and the second wavelength may be equal and the second beam splitter 340 may be replaced with a semitransparent mirror. When the first and the second wavelength are equal, the first illuminating optical system 200A and the second illuminating optical system 200B may be of the same configuration.

An eye characteristic measuring procedure to be carried out by the eye characteristic measuring apparatus 30000 will be described with reference to FIG. 12(*a*).

The eye characteristic measuring procedure is started in step S1. The alignment of the eye characteristic measuring apparatus with the eye is adjusted in step S2. In step S3, the control unit 610 controls the first driving unit 910 and the second driving unit 920 according to control signals provided by the arithmetic unit 600 to set the movable units at their initial positions; that is the first driving unit 910 moves the first illuminating optical system 200A to its initial position by driving a lens moving mechanism, and the second driving unit 920 moves the photodetecting optical system 300A to its initial position by driving a lens moving mechanism.

A measurement preparation procedure A is carried out in step S4. The measurement preparation procedure A is the same as that shown in FIG. 4 and described in connection with the first embodiment. The first state is set at the completion of the measurement preparation procedure A.

After the measurement preparation procedure A has been completed in step S4, a preparatory measurement procedure B-2 is executed in step S5. The preparatory measurement procedure B-2 will be described with reference to FIG. 13.

Figure 13:
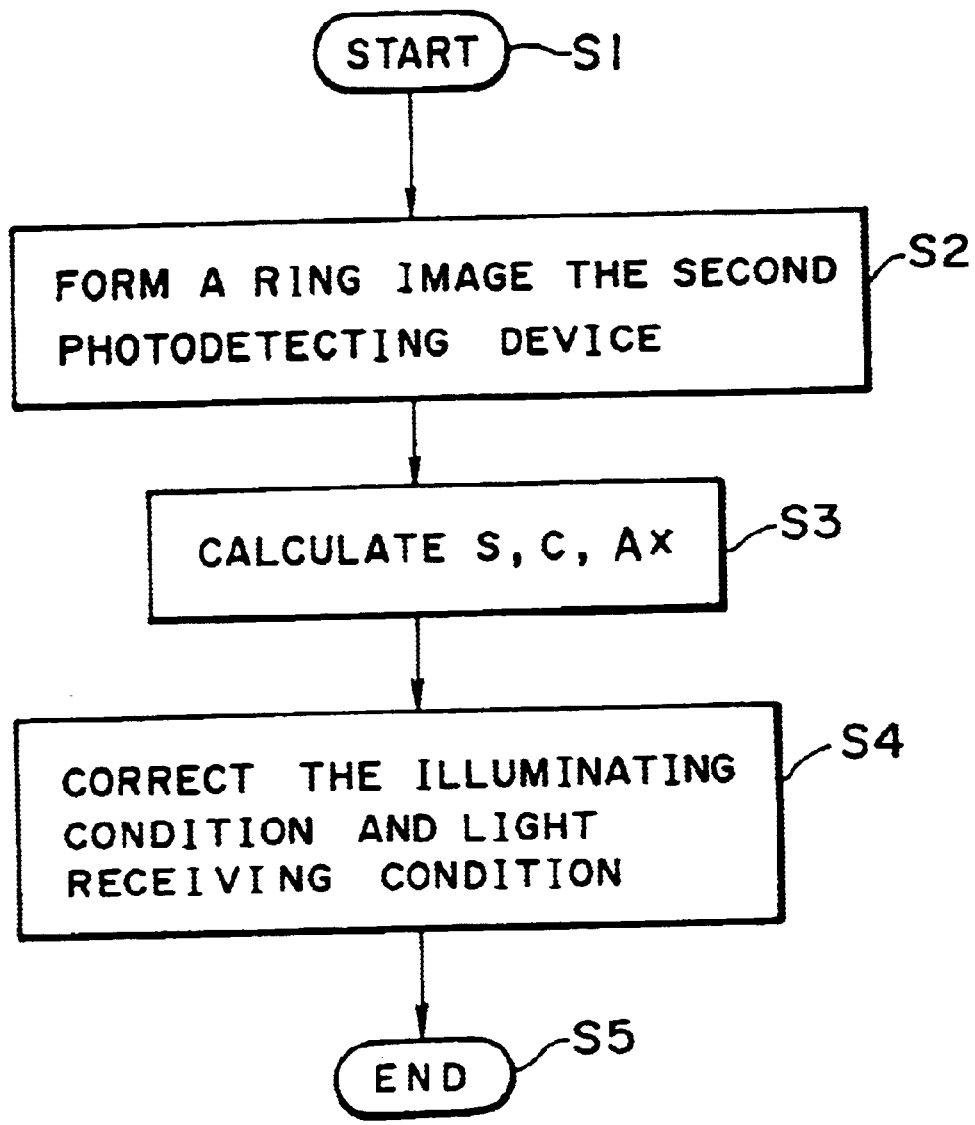
FIG. 13 is a flow chart of a preparatory measurement procedure B-2.

Referring to FIG. 13, the preparatory measurement procedure B-2 is started in step S1. In step S2, a ring image is formed on the second photodetecting device 520 by illuminating the pupil or the fundus by the second illuminating optical system 200B and detecting the reflected second light reflected from the retina of the eye 1000 by the second photodetecting device 520. When the fundus is illuminated, the ring image is an image of the second diaphragm ring 260.

In step S3, the arithmetic unit 600 calculates spherical power, cylindrical power and angle of astigmatic axis (S, C and Ax).

In step S4, the image forming condition changing unit is controlled according to the spherical power, cylindrical power and angle of astigmatic axis (S, C and Ax) calculated by the arithmetic unit 600 to correct the illuminating condition and the light receiving condition. This state corresponds to the second state.

In step S4, illuminating conditions and light receiving conditions are corrected and the preparatory measurement procedure B-2 is ended in step S5.

Referring again to FIG. 12(*a*), after the completion of the preparatory measurement procedure B-2 in step S5, a spot image is formed on the first photodetecting device 510 in step S6. The centroid of the spot image is determined in step S7. The centroid can be determined, for example, by projecting light on a plurality of pixels on the light receiving surface and measuring light intensities on the pixels. Thus, the position of the centroid can be measured in an accuracy not greater than $\frac{1}{10}$ of the element.

In step S8, dislocation of the measured centroid from an emmetropic centroid is calculated.

In step S9, Zernike factor is calculated by using Expressions (1) to (6), which will be described later.

In step S10, the calculated spherical power, cylindrical power, angle of astigmatic axis, spherical aberration, coma and other high-order aberration components. (S, C, Ax, SA, Coma and such) of the eye are displayed on the screen of the display unit 700.

A query is made in step S11 to see whether the eye characteristic measuring procedure has been completed. If the eye characteristic measuring procedure has been completed, the eye characteristic measuring procedure is ended in step S12. If the eye characteristic measuring procedure has not yet been completed, the eye characteristic measuring procedure returns to step S2.

Modification of the Third Embodiment

In the third embodiment, the image forming condition changing unit changes the image forming conditions of the first illuminating optical system 200A and the first photodetecting optical system 300A according to the level of the second signal provided by the second photodetecting device 520 to set the first changed state, and changes the image forming conditions of the first illuminating optical system 200A and the first photodetecting optical system 300A according to optical characteristics determined by the arithmetic unit 600 to set the second changed state.

In a modification of the third embodiment, the image forming condition changing unit changes the image forming conditions of the first illuminating optical system 200A and the first photodetecting optical system 300A according the optical characteristics determined by the arithmetic unit 600.

Figure 14A:
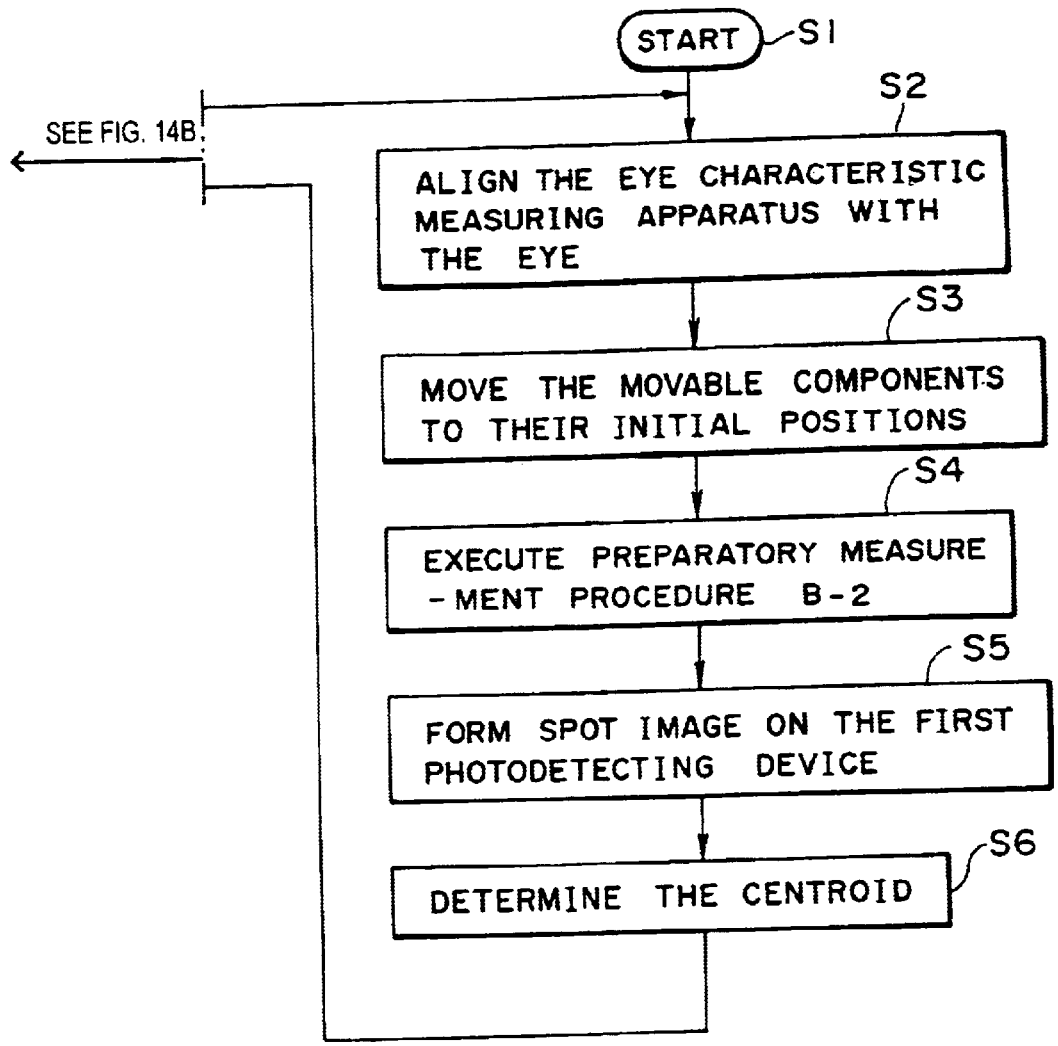
FIG. 14 is a flow chart of a measuring procedure to be carried out by an eye characteristic measuring apparatus in a modification of the eye characteristic measuring apparatus in the third embodiment.
Figure 14B:
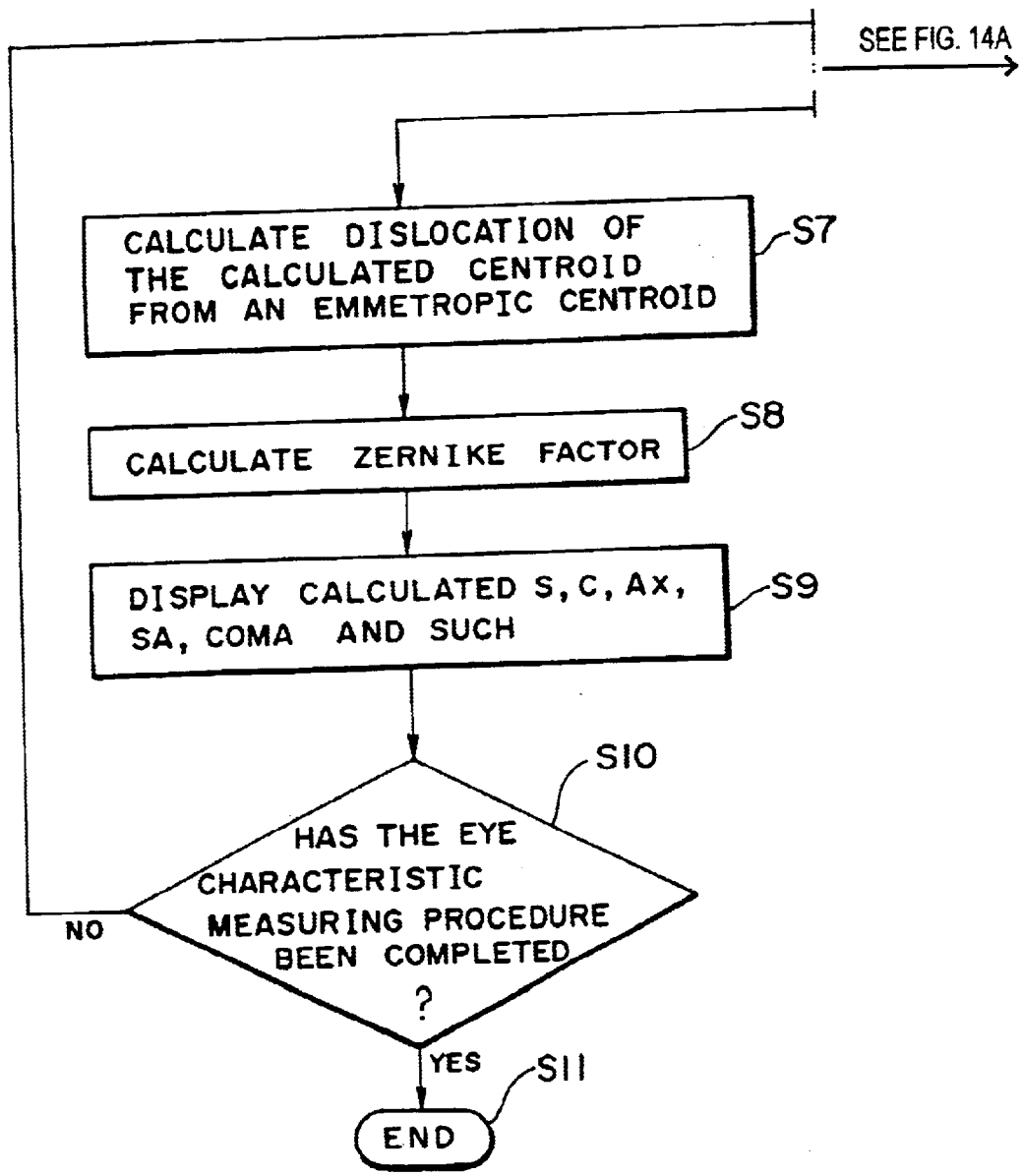

An eye characteristic measuring procedure to be carried out by the modification of the third embodiment will be described with reference to FIG. 14. The eye characteristic measuring procedure is started in step S1. The alignment of the eye characteristic measuring apparatus with the eye is adjusted in step S2. In step S3, the control unit 610 controls the first driving unit 910 and the second driving unit 920 according to control signals provided by the arithmetic unit 600 to set the movable units at their initial positions; that is the first driving unit 910 drives a lens moving mechanism to move the first cylindrical lens 220 of the first illuminating optical system 200A to its initial position. The second driving unit 920 drives a lens moving mechanism to move the second cylindrical lens 320 of the photodetecting optical system 300A to its initial position.

A preparatory measurement procedure B-2 is executed in step S4. The measurement preparation procedure B-2 is the same as the preparatory measurement procedure B-2 previously described with reference to FIG. 13 in connection with the third embodiment and hence the description thereof will be omitted.

Referring again to FIG. 14, after the completion of the preparatory measurement procedure B-2 in step S4, a spot image is formed on the first photodetecting device 510 in step S5. The centroid of the spot image is determined in step S6. The centroid can be determined, for example, by projecting light on a plurality of pixels on the light receiving surface and measuring light intensities on the pixels. Thus, the position of the centroid can be measured in an accuracy not greater than 1/10 of the element.

In step S7, dislocation of the measured centroid from an emmetropic centroid is calculated.

In step S8, Zernike factor is calculated by using Expressions (4) and (5), which will be described later.

In step S9, the calculated spherical power, cylindrical power, angle of astigmatic axis, spherical aberration, coma and other high-order aberration components. (S, C, Ax, SA, Coma and such) of the eye are displayed on the screen of the display unit 700.

A query is made in step S10 to see whether the eye characteristic measuring procedure has been completed. If the eye characteristic measuring procedure has been completed, the eye characteristic measuring procedure is ended in step S11. If the eye characteristic measuring procedure has not yet been completed, the eye characteristic measuring procedure returns to step S2.

The principle of operation of the arithmetic unit 600 for determining the optical characteristics of the eye 1000 on the basis of the first signal provided by the first photodetecting device 510 and corresponding to the inclination of light will be explained.

The present invention is intended to measure the wave aberration of the eye.

Figure 15:
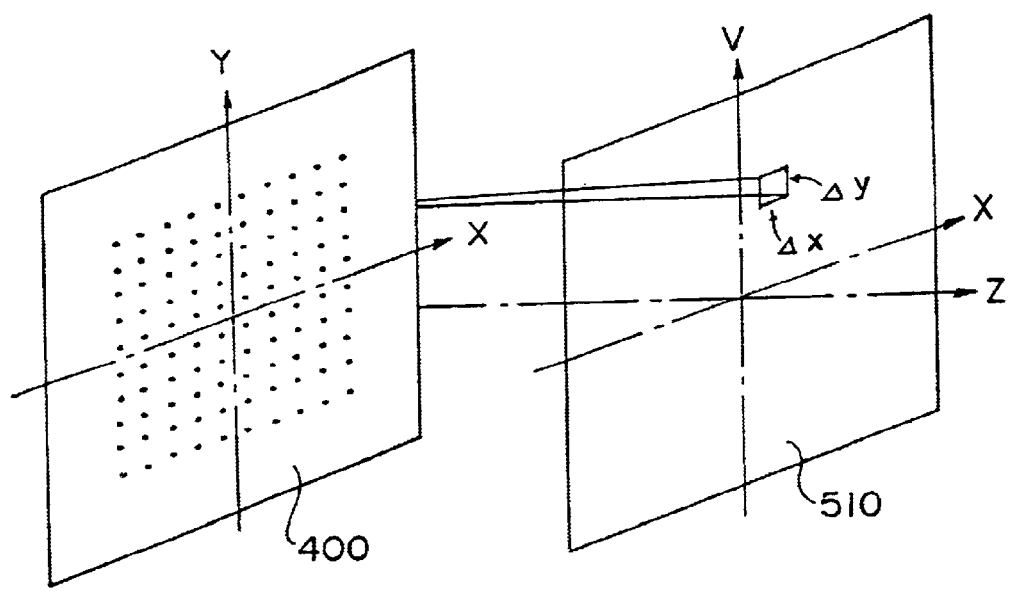
FIG. 15 is a diagrammatic view of assistance in explaining an optical characteristic calculating method.

As shown in FIG. 15, a coordinate system XY is defined by an x-axis and a Y-axis on the transforming device 400 and a coordinate system xy is defined by an x-axis and a y-axis on the first photodetecting device 510. A wavefront W(X, Y) expressed by Expression (3) is determined by Expressions (1) and (2)

$$\frac{\partial W(X, Y)}{\partial X} = \frac{\Delta x}{f} \quad \text{Expression (1)}$$

$$\frac{\partial W(X, Y)}{\partial Y} = \frac{\Delta y}{f} \quad \text{Expression (2)}$$

$$W(X, Y) = \sum_{i=0}^{n} \sum_{j=0}^{i} c_{ij} Z_{ij}(X, Y) \quad \text{Expression (3)}$$

Both sides of Expression (3) are differentiated by X and Y to obtain derivatives, and the derivatives are substituted into the left sides of Expressions (1) and (2) to obtain a polynomial of $C_{ij}$.

$Z_{ij}$ of Expression (3) is called Zernike polynomial expressed by Expressions (4) and (5).

$$Z_{nm} = R_n^{n-2m}(r)\left\{\begin{array}{c}\sin\\\cos\end{array}\right\}(n-2m)\theta \quad \text{Expression (4)}$$

where when n−2m>0, sin is applied
and when n−2m≦0, cos is applied $$R_n^{n-2m}(r) = \sum_{S=0}^{m} (-1)^S \frac{(n-S)!}{S!(m-S)!(n-m-S)!} r^{n-2S} \quad \text{Expression (5)}$$

Unknowns $C_{ij}$ are determined by reducing the mean square error of Expression (6) to a minimum.

$$S(x) = \sum_{i=1}^{\text{data number}} \left[\left\{\frac{\partial W(X_i, Y_i)}{\partial X} - \frac{\Delta x_i}{f}\right\}^2 + \left\{\frac{\partial W(X_i, Y_i)}{\partial Y} - \frac{\Delta y_i}{f}\right\}^2\right] \quad \text{Expression (6)}$$

The $C_{ij}$ thus determined are important optical parameters of the eye.

Figure 16:
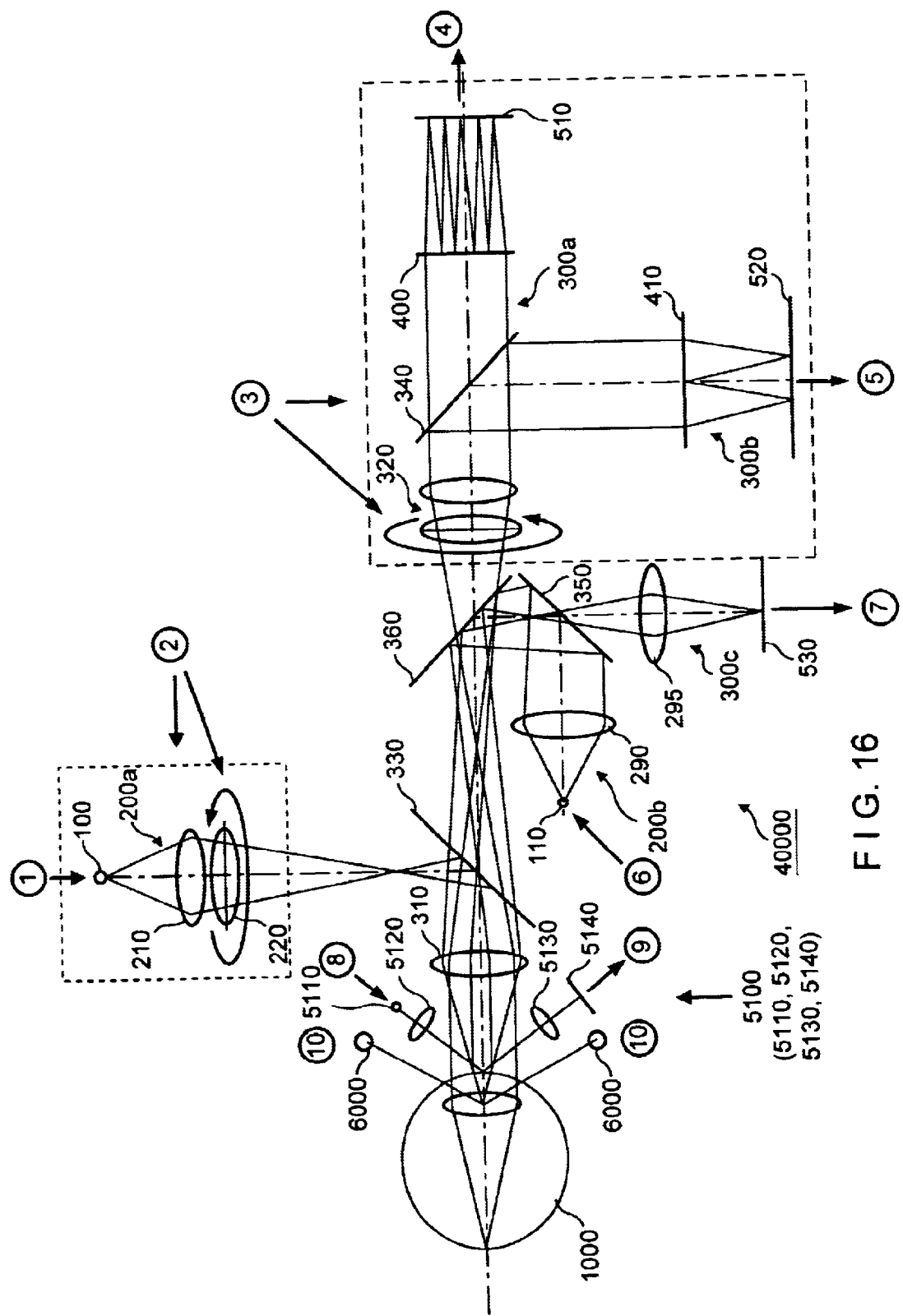
FIG. 16 is a diagrammatic view of an eye characteristic measuring apparatus in a fourth embodiment according to the present invention.

In Zernike polynomial, symbols indicate the followings.
$Z_{10}, Z_{11}$: Prisms
$Z_{21}$: S
$Z_{20}, Z_{22}$: C, Ax
$Z_{30}, Z_{33}$: Arrow aberration
$Z_{31}, Z_{32}$: Third-order coma aberration
$Z_{42}$: Third-order spherical aberration
$Z_{41}, Z_{43}$: Astigmatism
$Z_{52}, Z_{53}$: Fifth-order coma aberration
$Z_{63}$: Fifth-order spherical aberration
$Z_{84}$: Seventh-order spherical aberration Fourth Embodiment Referring to FIG. 16, an eye characteristic measuring apparatus 40000 in a fourth embodiment according to the present invention includes a first light source 100 that emits first light of a first wavelength, a first illuminating optical system 200A that illuminates a small region of the retina of the eye with the first light emitted by the first light source 100, a first photodetecting optical system 300A that guides part of the reflected light reflected from the retina of the eye through a first transforming member 400 that divides the reflected light into at least seventeen light beams to a first photodetecting device 510, a second photodetecting optical system 300B that guides part of reflected second light reflected from the retina of the eye through a second transforming member 410 that divides the reflected light into at least four light beams to a second photodetecting device 520, an anterior segment illuminating light source 110 that emits light of a second wavelength for illuminating an anterior segment of the eye, an anterior segment illuminating optical system 200B that illuminates a predetermined region of an anterior segment of the eye with the light emitted by the anterior segment illuminating light source 110, a third photodetecting optical system 300C that guides the light reflected from the anterior segment of the eye to an anterior segment photodetecting device 530, an arithmetic unit 600 that determines the optical characteristics of the eye on the basis of a first signal provided by the first photodetecting device 510 and corresponding to the inclination of the light and determines the illuminating conditions of the first illuminating optical system 200A on the basis of a second signal provided by the second photodetecting device 520, and an image forming condition changing unit that changes the image forming conditions of the first illuminating optical system 200A and the first photodetecting optical system 300A according to the level of the second signal provided by the second photodetecting device 520 to set a first changed state and changes the image forming conditions of the first illuminating optical system 200A and the first photodetecting optical system 300A according to the optical characteristics determined by the arithmetic unit 600 to set a second changed state.

The second illuminating optical system 200B illuminates the predetermined region of the anterior segment of the eye with the second light emitted by the second light source 110. The second illuminating optical system 200B includes the second light source 110, a fifth condenser lens 290, a fourth beam splitter 350, a fifth beam splitter 360, a first beam splitter 330 and a first afocal lens 310.

A Z-alignment optical system 5100 includes a fourth light source 5110, a collimator lens 5120, a condenser lens 5130 and a fourth photodetecting device 5140.

An alignment adjusting operation to be carried out by an alignment adjusting optical system will be described. The alignment adjusting operation adjusts the positional relation between the eye and the eye characteristic measuring apparatus with respect to a direction perpendicular to the optical axis by using the light emitted by the second light source 110 and reflected by the anterior segment of the eye.

The light emitted by the second light source 110 is guided through the fifth condenser lens 290, the fourth beam splitter 350, the fifth beam splitter 360 and the first afocal lens 310 to illuminate the eye with substantially parallel light rays. Reflected light reflected from the cornea of the eye diverges in divergent light rays as if the light rays are emitted from a point at half the radius of curvature of the cornea the divergent light rays are converged by the first afocal lens 310 and sixth condenser lens 295 in a spot image on the anterior segment photodetecting device 530.

If the spot image formed on the anterior segment photodetecting device 530 is dislocated from the optical axis, the eye characteristic measuring apparatus is moved in a plane perpendicular to the optical axis. When the spot image lies on the optical axis on the anterior segment photodetecting device 530, the eye characteristic measuring apparatus is aligned with the eye.

The wavelength of the second light emitted by the second light source 110 is longer than that of the first light emitted by the first light source 100 and is, for example, 940 nm. A dichroic mirror that transmits the first light emitted by the first light source 100 and reflects the second light emitted by the second light source 110 is used as the second beam splitter 340 to prevent the first light and the second light from falling on the wrong optical systems, respectively, to generate noise.

When the anterior segment of the eye is illuminated with light emitted by illuminating light sources 6000, an image of the eye is formed on the anterior segment photodetecting device 530. The image of the eye may be used for alignment adjustment; the position of the eye characteristic measuring apparatus relative to the eye is adjusted so that the center of the pupil of the eye coincides with the optical axis.

Operating distance adjustment is achieved by emitting parallel light rays by the fourth light source 5110 along the optical axis toward the eye, and receiving the reflected light reflected from the eye through the condenser lens by the fourth photodetecting device 5140.

When the eye is at an appropriate operating distance, a spot image of the fourth light source 5110 is formed at a position on the fourth photodetecting device 5140 where the optical axis intersects the fourth photodetecting device 5140. If the eye is not at the appropriate operating distance, the spot image deviates vertically from the position on the fourth photodetecting device 5140 where the optical axis intersects the fourth photodetecting device 5140.

Figure 17:
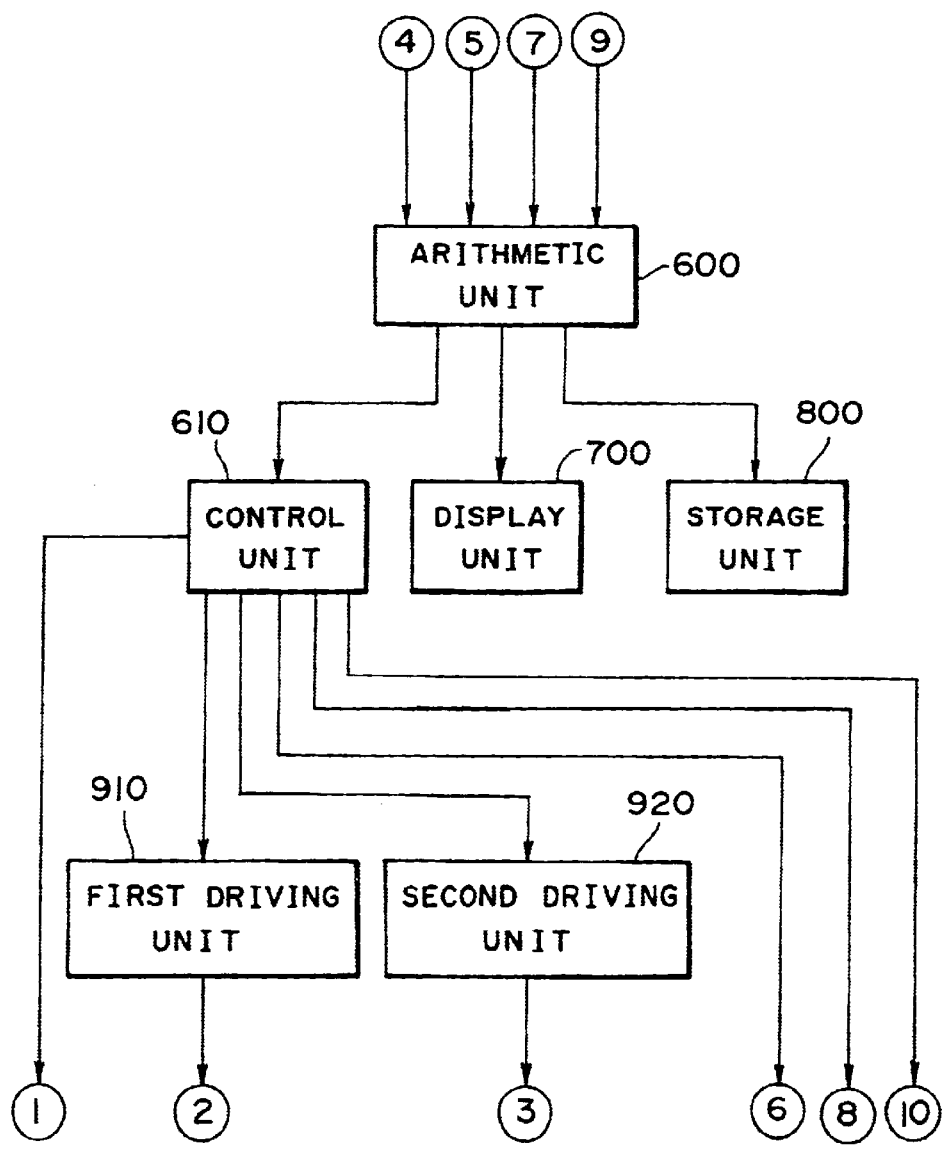
FIG. 17 is a block diagram of an electrical system included in the eye characteristic measuring apparatus in the fourth embodiment.

An electrical system included in the eye characteristic measuring apparatus 40000 will be described with reference to FIG. 17. An arithmetic unit 600 included in the electrical system receives signals from the second photodetecting device 520, the third photodetecting device 530 and the fourth photodetecting device 5140 in addition to the signal received by the arithmetic unit 600 shown in FIG. 2. A control unit 610 included in the electrical system controls additionally the second light source 110, the fourth light source 5110 and the illuminating light sources 6000. The electrical system is the same in other respects as that of the second embodiment and hence the further description thereof will be omitted.

An eye characteristic measuring procedure to be carried out by the eye characteristic measuring apparatus 40000 will be described with reference to FIG. 18. The eye characteristic measuring procedure is similar to that shown in FIG. 3, except that a step S41 for a preparatory measurement procedure B-3 is interposed between steps S4 and S5.

The principle of measurement will be described. The second photodetecting optical system 300B including the second transforming device 410 carries out coarse measurement (second state). The first photodetecting optical system 300A including the first transforming device 400 carries out precise measurement (first state). Thus, measurement can be achieved in a shorter time.

The preparatory measurement procedure B-3 will be explained with reference to FIG. 19.

The first transforming device 400 divides the first reflected light into at least seventeen light beams. The second transforming device divides the second reflected light into at least four light beams.

The second transforming device 410 is provided with four lenses 411. The respectively foci of the lenses 411 are determined so that the positions of images formed by the lenses 411 of the second transforming device 410 coincide substantially with that of an image formed by the second transforming device 410.

Figure 20:
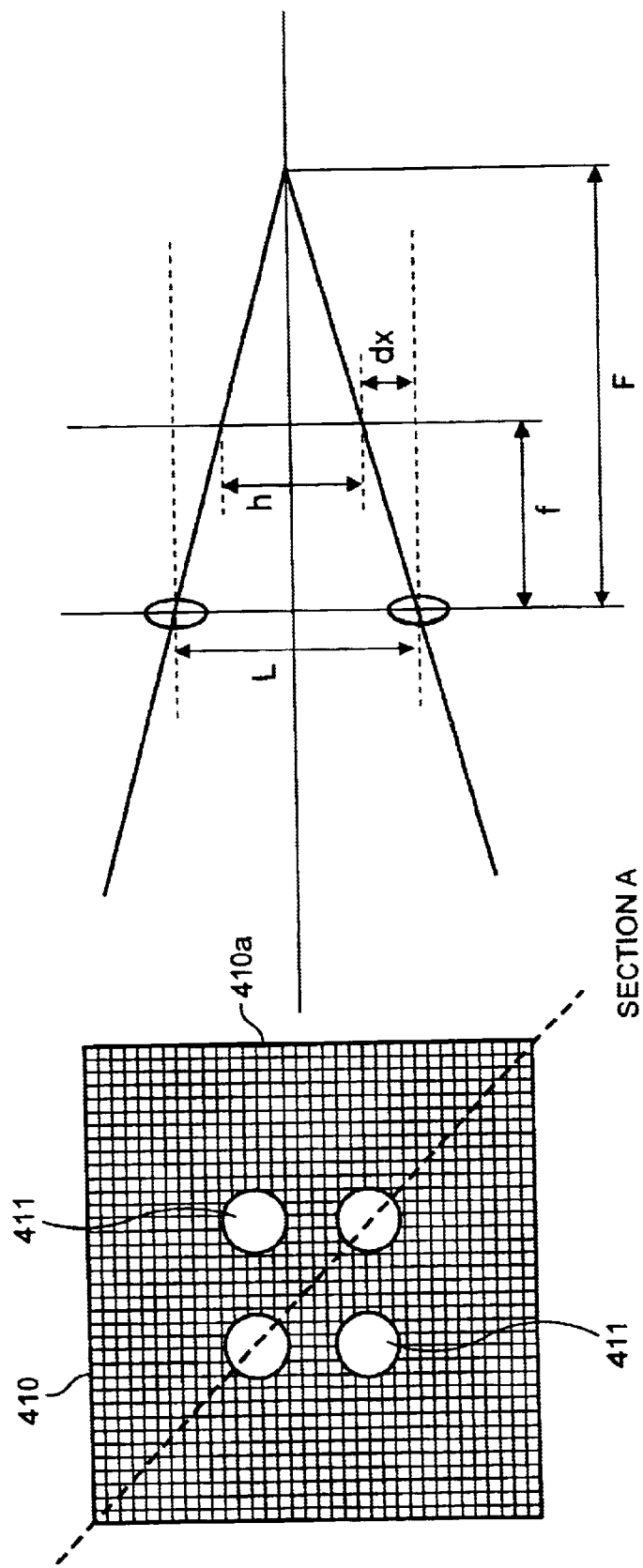
FIG. 20 is a diagrammatic view of assistance in explaining the principle of measurement.

Therefore, as shown in FIG. 20, spherical power D is expressed by:

$$D=(1/F)\cdot(1/M)$$

where M is magnification between the pupil of the eye and the second transforming device 410.

$$dx=(L-h)/2$$

Therefore, $$F=(L/2)/(dx \cdot f)$$

and thus the spherical power D can be determined.

Figure 21:
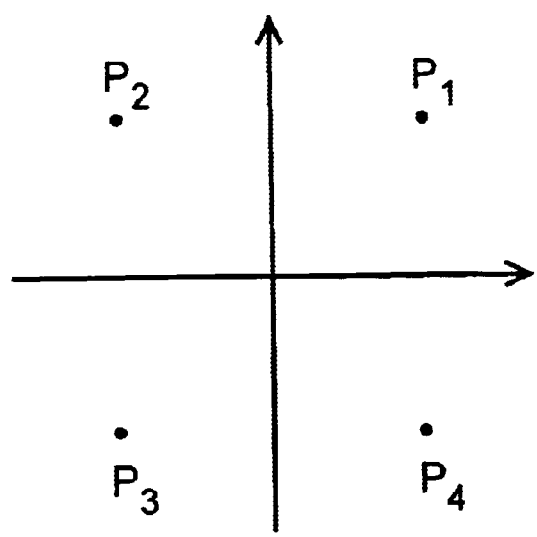
FIG. 21 is a diagrammatic view of assistance in explaining the principle of measurement.

As shown in FIG. 21, distances are expressed by:

$$|P_2P_4|=\{(P_{2x}-P_{4x})^2+(P_{2y}-P_{4y})^2\}^{0.5}$$

$$|P_1P_3|=\{(P_{1x}-P_{3x})^2+(P_{1y}-P_{3y})^2\}^{0.5}$$

Therefore, $$h=(|P_2P_4|+|P_1P_3|)/2$$

Figure 19:
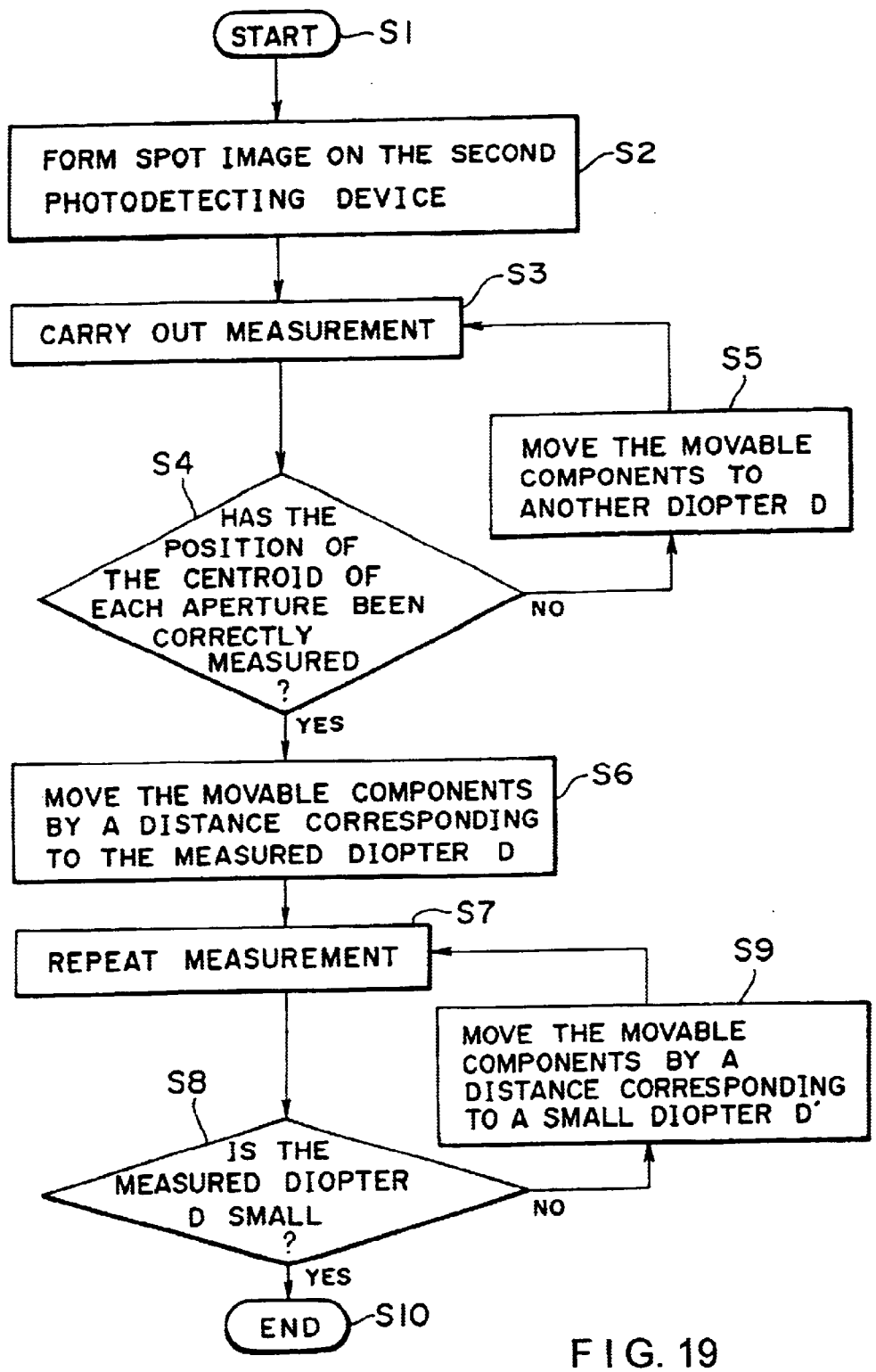
FIG. 19 is a flow chart of a preparatory measurement procedure B-3.

As shown in FIG. 19, the preparatory measurement procedure B-3 is started in step S1, a spot image is formed on the second photodetecting device 520 in step S2 and the measurement is carried out in step s3.

A query is made in step S4 to see whether the position of the centroid of each aperture are measured correctly in step S3. If the response in step S4 is negative, the movable components are moved to another diopter D in step S5 and the procedure returns to step S3. If the response in step S4 is affirmative, the movable components are moved by a distance corresponding to the measured diopter D in step S6. Measurement is repeated in step S7. A query is made in step S8 to see whether the measured diopter D is small. If the response in step S8 is negative, the movable components are moved by a distance corresponding to a small diopter D' in the direction of the sign of the measured diopter D in step S9 and the procedure returns to step S7.

If the response in step S8 is affirmative, the preparatory measurement procedure B-3 is ended in step S10.

Figure 18B:
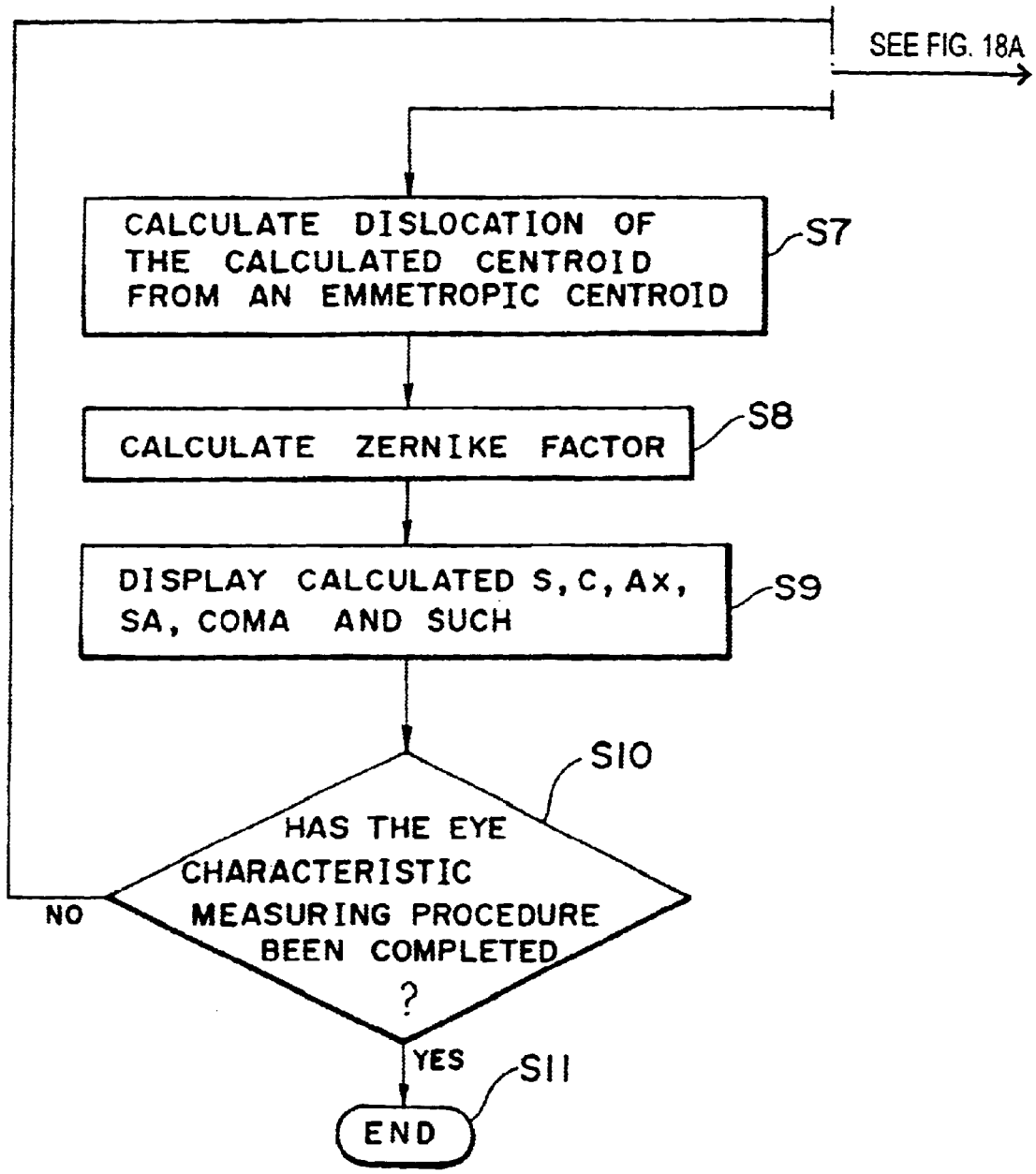
FIG. 18 is a flow chart of a measuring procedure to be carried out by the eye characteristic measuring apparatus in the fourth embodiment.

As shown in FIG. 18, the preparatory measurement procedure B-3 is carried out in step S41. The preparatory measurement procedure B-3 is the same in other respects as the procedure shown in FIG. 3 and hence the further description thereof will be omitted. The measurement preparation procedure A to be carried out in step S4 may be omitted.

Modification of the Fourth Embodiment

Figure 22:
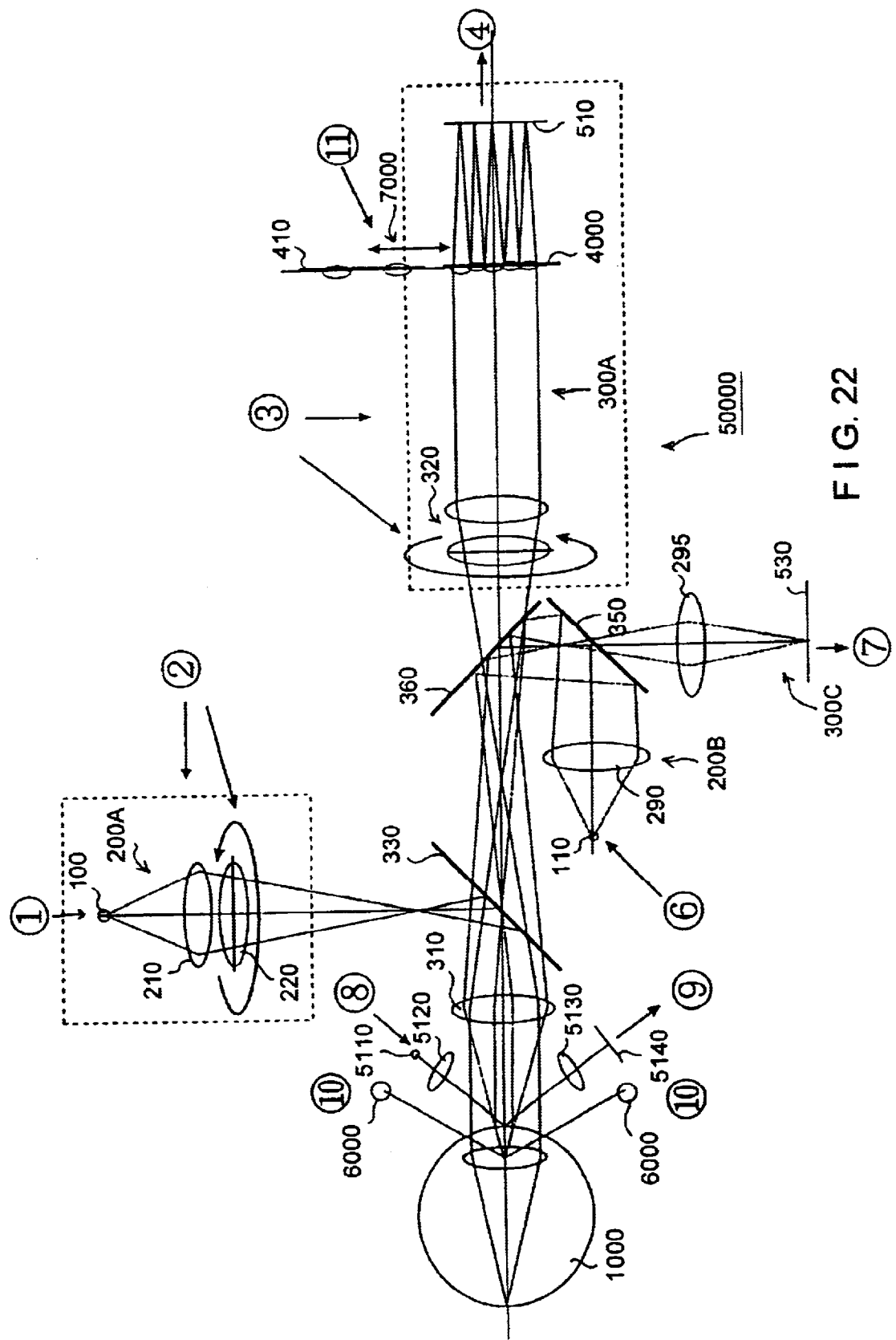
FIG. 22 is a diagrammatic view of an eye characteristic measuring apparatus in a modification of the eye characteristic measuring apparatus in the fourth embodiment.

An eye characteristic measuring apparatus in a modification of the fourth embodiment will be described with reference to FIGS. 22 and 23. The eye characteristic measuring apparatus in the modification is not provided with any optical system corresponding to the second photodetecting optical system 300B, and the first transforming device 400 or the second transforming device 410 can be selectively inserted in the first photodetecting optical system 300A. The first transforming device 400 is used for precise measurement and the second transforming device 410 is used for rough measurement.

The first photodetecting optical system 300A is provided with a changing mechanism 7000 for selectively inserting the first transforming device 400 or the second transforming device 410 into the first photodetecting optical system 300A. As shown in FIG. 23, the changing mechanism 7000 is driven by a third driving unit 930.

Figure 3B:
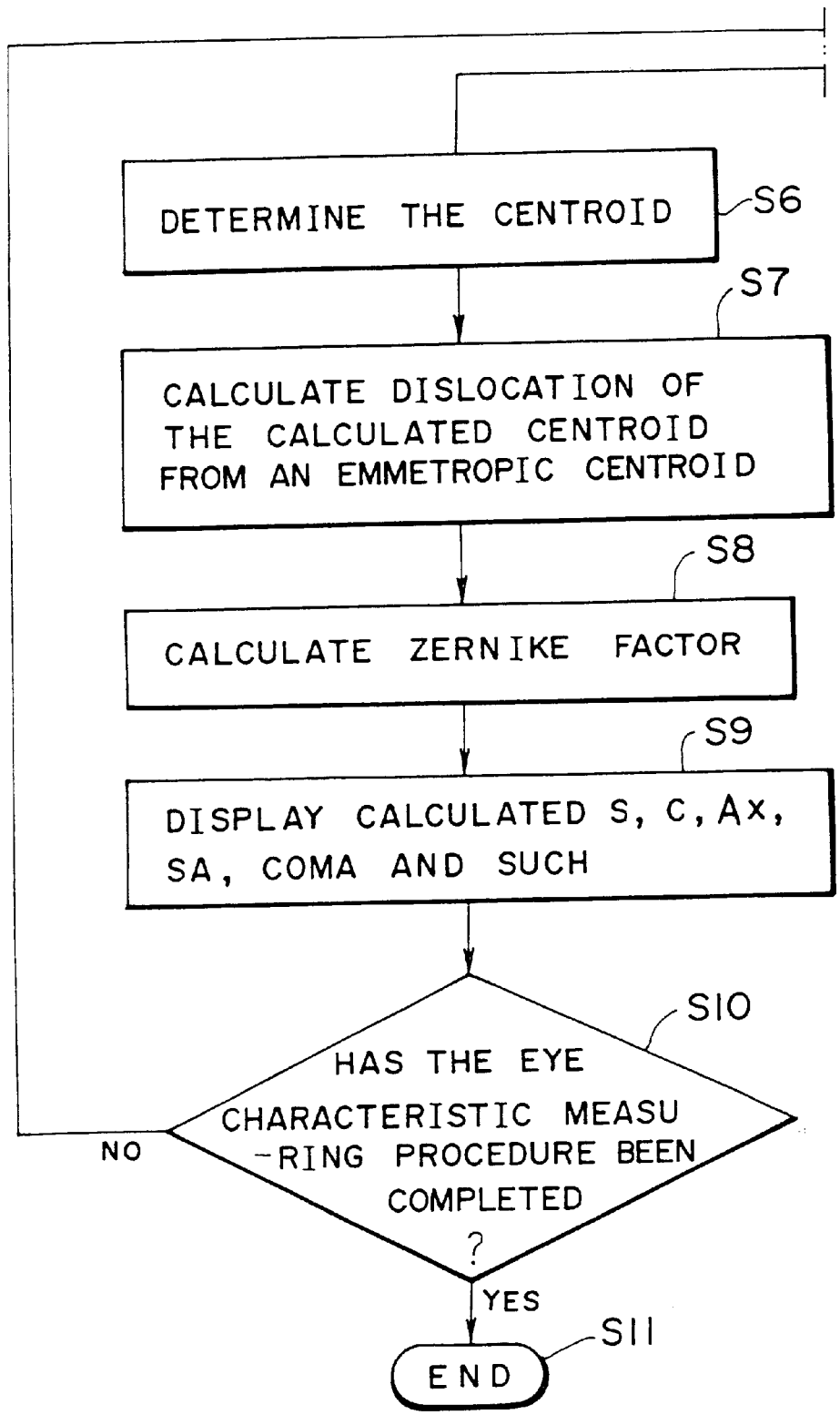
FIG. 3 is a flow chart of an eye characteristic measuring procedure to be carried out by the eye characteristic measuring apparatus in the first embodiment.
Figure 24A:
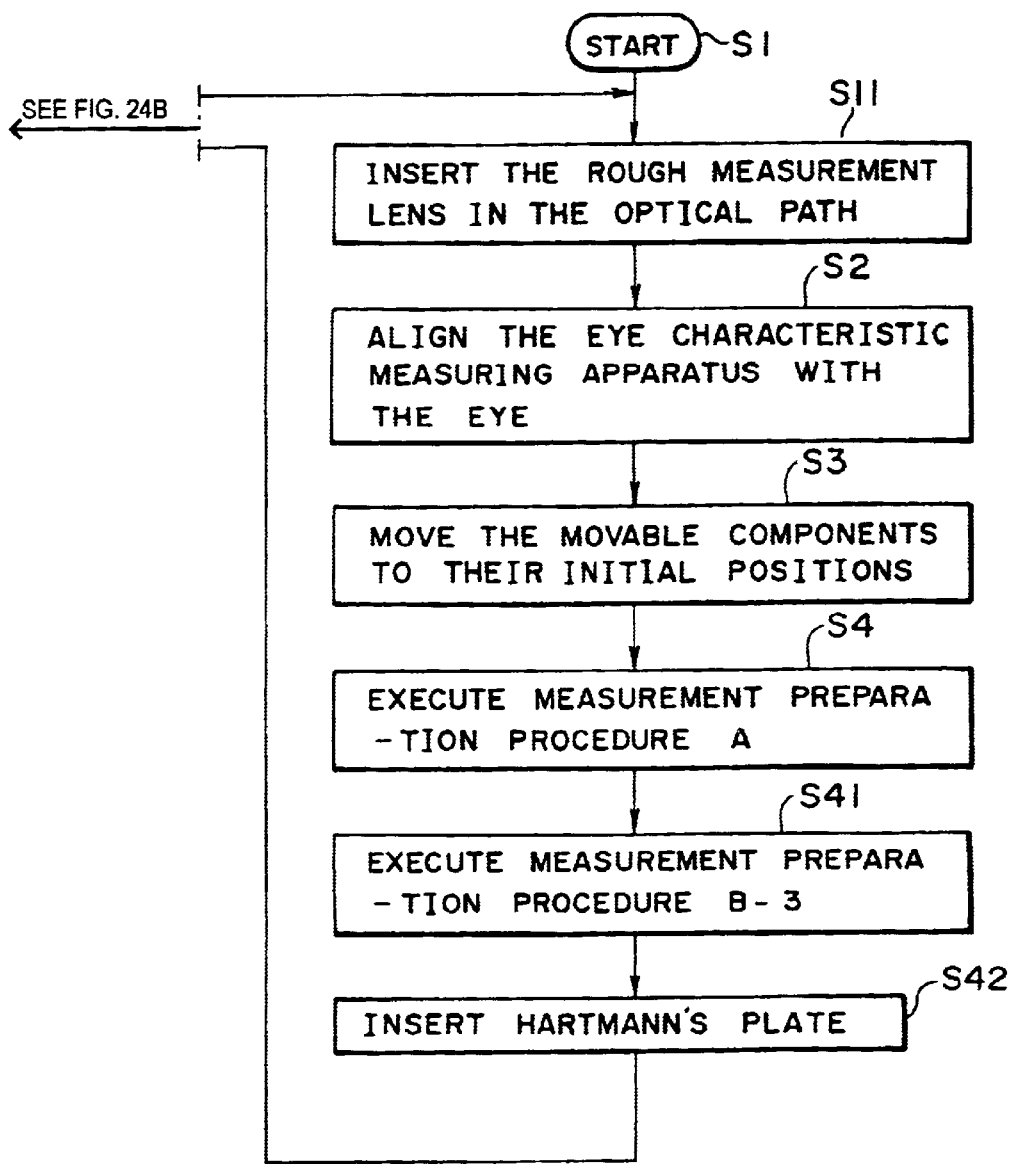
FIG. 24 is a flow chart of a measuring procedure to be carried out by the eye characteristic measuring apparatus in the modification of the eye characteristic measuring apparatus in the fourth embodiment.
Figure 24B:
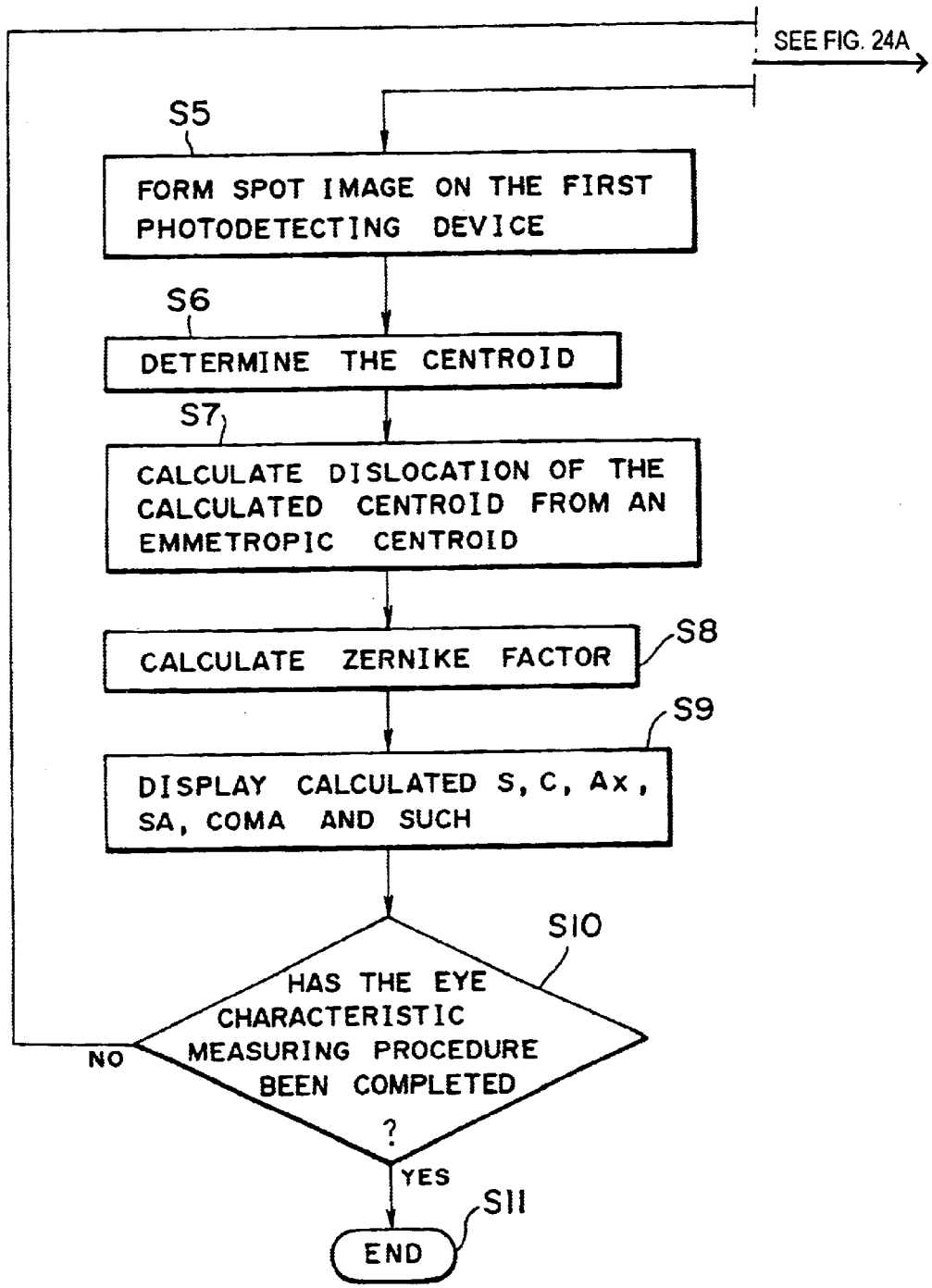

An eye characteristic measuring procedure shown in FIG. 24 is similar to that shown in FIG. 3, except that step S11 for rough measurement lens insertion is interposed between steps S1 and S2, step S41 for preparatory measurement procedure B-3 is interposed between step S4 and S5, and the eye characteristic measuring procedure includes an additional step S42 for Hartmann's plate insertion.

In step S11, the changing mechanism 7000 inserts the second transforming device 410 in the optical path for rough measurement. The same preparatory measurement procedure B-3 as that carried out by the fourth embodiment is carried out in step S41. I step S42, the changing mechanism 7000 inserts the first transforming device 400 for precise measurement.

The modification of the fourth embodiment is the same in measuring function, construction and operation as the foregoing embodiments and hence the further description thereof will be omitted.

The second transforming device 410 may be provided with apertures 410a greater than those of the first transforming device 400. The apertures 410a of the second transforming device 410 maybe arranged t intervals greater than those at which the apertures of the first transforming device 400 are arranged.

In the second state (rough measurement), the number of the light beams may be smaller than that of the light beams for the first state (precise measurement).

In the second state (rough measurement), a mask for reducing the number of the light beams may be disposed near the first transforming device 400. In the second state (rough measurement), a mask that does not make the reflected light pass through the adjacent apertures may be disposed near the first transforming device 400.

According to the present invention, the eye characteristic measuring apparatus comprises the first light source that emits the light of the first wavelength, the first illuminating optical system capable of illuminating a small region of the retina of the eye in a variable illuminating condition, the first photodetecting optical system provided with the first photodetecting device that receives part of the reflected light reflected from the retina through the first transforming device that divides the reflected light beam into at least seventeen light beams, the arithmetic unit that determines the optical characteristics of the eye on the basis of the first signal provided by the first photodetecting device and corresponding to the inclination of the light beam, and the image forming condition changing unit that changes the respective image forming conditions of the first illuminating optical system and the first photodetecting optical system according to the level of the first signal provided by the first photodetecting device. The image forming condition changing unit sets optimum illuminating and light receiving conditions, so that the optical characteristics of the eye can be highly accurately measured.

What is claimed is:

1. An eye characteristic measuring apparatus comprising:
    a first light source that emits light of a first wavelength;
    a first illuminating optical system capable of illuminating a small region of the retina of an eye in a variable illuminating condition with the light emitted by the first light source;
    a first photodetecting optical system provided with a first transforming device that divides reflected light reflected from the retina of the eye into a least seventeen light beams and a first photodetecting device that receives part of the reflected light reflected from the retina through the first transforming device;
    an arithmetic unit that determines optical characteristics of the eye on the basis of a first signal provided by the first photodetecting device and corresponding to inclination of the transforming light from transform device; and
    an image forming condition changing unit that changes respective image forming conditions of the first illuminating optical system and the first photodecting optical system according to the first signal provided by the first photodetecting device to set a first changed state and changes respective image forming conditions of the first illuminating optical system and the first photodetecting optical system according to optical characteristics determined by the arithmetic unit to set a second changed state.

2. An eye characteristic measuring apparatus comprising:
    a first light source that emits light of a first wavelength;
    a first illuminating optical system capable of illuminating a small region of the retina of an eye in a variable illuminating condition with the light emitted by the first light source;
    a first photodetecting optical system provided with a first transforming device that divides reflected light reflecting from the retina of the eye into at least seventeen light beams and a first photodetecting device that receives part of reflected light reflected from the retina through the first transforming device;
    a second photodetecting optical system provided with a second photodetecting device that receives second light reflected from the retina of the eye;

an arithmetic unit that determines optical characteristics of the eye n the basis of a first signal provided by the first photodetecting device and corresponding to inclination of the transforming light from transform device; and an image forming condition changing unit that changes respective image forming conditions of the first illuminating optical system and the first photodetecting optical system according to a least a second signal provided by the second photodetecting device.

3. The eye characteristic measuring apparatus according to claim 2, wherein the image forming condition changing unit changes the image forming conditions of the first illuminating optical system and the first photodetecting optical system according to a level of the second signal provided by the second photodetecting device to set a first state, and then changes the image forming conditions of the first illuminating optical system and the first photodetecting optical system according to optical characteristics determined by the arithmetic unit to set a second state.

4. The eye characteristic measuring apparatus according to claim 2, wherein the image forming condition changing unit changes the image forming conditions of the first illuminating optical system and the first photodetecting optical system according to the second signal provided by the second photodetecting device to set a first state, and then changes the image forming conditions of the first illuminating optical system and the first photodetecting optical system according to a signal provided by the first photodetecting device upon the reception of light to set a second state.

5. An eye characteristic measuring apparatus comprising:
a first light source that emits light of a first wavelength;
a first illuminating optical system capable of illuminating a small region of the retina of an eye in a variable illuminating condition with the light emitted by the first light source;
a first photdetecting optical system provided with a first transforming device that divides reflected light reflected from the retina of the eye into at least seventeen light beams and a first photodetecting device that receives part of the reflected light reflected from the retina through the first transforming device;
a second light source that emits light of a second wavelength;
a second illuminating optical system capable of illuminating a predetermined region of the retina of the eye in a variable illuminating condition with the light emitted by the second light source;
a second photodetecting optical system provided with a second photodetecting device that receives reflected light of the second wavelength reflected from the retina;
an arithmetic unit that determines optical characteristics of the eye on the basis of a first signal provided by the first photodetecting device and corresponding to inclination of the transforming light from transform device and determines the optical characteristics of the eye on the basis of a second signal provided by the second photodetecting device; and
an image forming condition changing unit that changes respective image forming conditions of the first illuminating optical system and the first photodetecting optical system according to the optical characteristics determined by the arithmetic unit.

6. An eye characteristic measuring apparatus comprising;
a first light source that emits light of a first wavelength;

a first illuminating optical system capable of illuminating a small region of the retina of an eye in a variable illuminating condition with the light emitted by the first light source;
a first photodetecting optical system provided with a first transforming device that divides reflected light reflected from the retina of the eye into a least seventeen light beams and a first photodetecting device that receives part of the reflected light reflected from the retina through the first transforming device;
a second light source that emits light of a second wavelength;
a second illuminating optical system capable of illuminating a predetermined region of the retina of the eye in a variable illuminating condition with the light of the second wavelength emitted by the second light source;
a second photodetecting optical system provided with a second photodetecting device that receives reflected light of the second wavelength reflected from the retina;
an arithmetic unit that determines optical characteristics of the eye on the basis of a first signal provided by the first photodecting device and corresponding to inclination of the transforming light from transform device and detects illuminating conditions of the first illuminating optical system on the basis of a second signal provided by second photodecting device; and
an image forming condition changing unit that changes respective image forming conditions of the first illuminating optical system and the first photodetecting optical system according to a level of a first signal provided by the first photodetecting device to set a first change state, and changes respective image forming conditions of the first illuminating optical system and the first photodetecting optical system according to the optical characteristics determined by the arithmetic unit to a second changed state.

7. An eye characteristic measuring apparatus comprising:
a first light source that emits light of a first wavelength;
a first illuminating optical system capable of illuminating a small region of the retina of an eye in a variable illuminating condition with the light emitted by the first light source;
a first photodetecting optical system provided with a first transforming device that divides first reflected light reflected from the retina of the eye into a least seventeen light beams and a first photodetecting device that receives part of the reflected light reflected from the retina through the first transforming device;
a second photodetecting optical system provided with a second transforming device that divides second reflected light reflected from the retina of the eye into at least four light beams and a second photodetecting device that receives part of the second reflected light reflected from the retina through the second transforming device;
an arithmetic unit that determines optical characteristics of the eye on the basis of a first signal provided by the first photodetecting device and corresponding to inclination of the transforming light from transform device; and
an image forming condition changing unit that changes respective image forming conditions of the first illuminating optical system and the first photodetecting optical system according to a level of a second signal provided by the second photodetecting device.

8. An eye characteristic measuring apparatus comprising:

a first light source that emits light of a first wavelength;

a first illuminating optical system capable of illuminating a small region of the retina of an eye in a variable illuminating condition with the light emitted by the first light source;

a first photodetecting optical system provided with a first transforming device that divides first reflected light reflected from the retina of the eye into at least seventeen light beams with first aperture and a first photodetecting device that receives the reflected light reflected from the retina through the first transforming device;

a second photodetecting optical system provided with a second transforming device that divides second reflected light reflected from the retina of the eye into at least four light beams with second aperture greater than those of first transforming device and a second photodetecting device that receives the second reflected light reflected from the retina through the second transforming device;

an arithmetic unit that determines optical characteristics of the eye on the basis of a second signal provided by the second photodetecting device; and an image forming condition changing unit that changes respective image forming conditions of the first illuminating optical system and the first photodetecting optical system according to the optical characteristics determined by the arithmetic unit.

9. The eye characteristic measuring apparatus according to claim 6 or 8, wherein the image forming condition changing unit changes the image forming conditions of the first illuminating optical system and the first photodetecting optical system according to the level of the second signal provided by the second photodetecting device or the optical characteristics determined on the basis of the second signal, and then changes the image forming conditions of the first illuminating optical system and the first photodetecting optical system according to the level of the first signal provided by the second photodetecting device or the optical characteristics determined on the basis of the first signal.

10. An eye characteristic measuring apparatus comprising:

a first light source that emits light of a first wavelength;

a first illuminating optical system capable of illuminating a small region of the retina of an eye in a variable illuminating condition with the light emitted by the first light source;

a first photodetecting optical system provided with a first transforming device that dives first reflected light reflected from the retina of the eye into at least seventeen light beams with first aperture and a first photodetecting device that receives the reflected light reflected from the retina through the first transforming device;

a second photodetecting optical system provided with a second transforming device that divides second reflected light reflected from the retina of the eye into at least four light beams with second aperture greater than those of the first transforming device and a second photodetecting device that receives the second reflected light through the second transforming device;

an arithmetic unit that determines optical characteristics of the eye on the basis of a first signal provided by the first photodetecting device and corresponding to an inclination of the transforming light from transform device and determines illuminating conditions of the first illuminating optical system; and an image forming condition changing unit that changes respective image forming conditions of the first illuminating optical system and the first photodetecting optical system according to a level of a second signal provided by the second photodetecting device to set a first changed state, and then changes image forming conditions of the first illuminating optical system and the first photodetecting optical system according to the optical characteristics determined by the arithmetic unit to set a second changed state.

11. An eye characteristic measuring apparatus comprising:

a first light source that emits light of a first wavelength;

a first illuminating optical system capable of illuminating a small region of the retina of an eye in a variable illuminating condition with the light emitted by the first light source;

a first photodetecting optical system for setting a first state where reflected light reflected from the retina of the eye is guided through a first transforming device that divides the reflected light into at least seventeen light beams to a first photodetecting device and a second state where the reflected light is guided through a second transforming device that divides the reflected light into a number of light beams less than that of the light beam provided by the first transforming device to a second photodetecting device;

an image forming condition changing unit that changes respective image forming conditions of the first illuminating optical system and the first photodetecting optical system on the basis of a second signal provided by the first photodetecting device in the second state; and an arithmetic unit that determines optical characteristics of the eye on the basis of a first signal provided by the first photodetecting device in the first state.

12. The eye characteristic measuring apparatus according to claim 11, wherein the second transforming device is provided with an aperture, the first transforming device is provided with an aperture, and the aperture of the second transforming device is greater than that of the first transforming device.

13. The eye characteristic measuring apparatus according to claim 11 or 12, wherein the second transforming device is provided with apertures, the first transforming device is provided with apertures, and intervals between the apertures of the second transforming device are greater than those of the apertures of the first transforming device.

14. The eye characteristic measuring apparatus according to claim 13 or 12, wherein the second transforming device is provided with a plurality of lenses, the first transforming device is provided with a plurality of lenses, and respective focal lengths of the lenses are determined so that positions of images formed by the plurality of lenses of the first transforming device coincide with those of images formed by the plurality of lenses of the second transforming device.

15. An eye characteristic measuring apparatus comprising:

a first light source that emits light of a first wavelength;

a first illuminating optical system capable of illuminating a small region of the retina of an eye in a variable illuminating condition with the light emitted by the first light source;

a first photodetecting optical system capable of setting a first state in which reflected light reflected from the retinal of the eye is divided into at least seventeen light beams and a second state in which the reflected light is divided into a number of light beams smaller than that of light beams formed in the first state;

an image forming condition changing unit that changes respective image forming conditions of the first illuminating optical system and the first photodetecting optical system on the basis of a second signal provided by the first photodetecting device in the second state; and an arithmetic unit that determines optical characteristics of the eye on the basis of a first signal provided by the first photodetecting device in the first state.

16. The eye characteristic measuring apparatus according to claim 15, wherein the first state is set by a first transforming device that divides reflected light reflected from the retina of the eye into at least seventeen light beams, and the second state is set by inserting a mask at a position near the first transforming device in an optical path to reduce the number of the light beams formed by the first transforming device.

17. The eye characteristic measuring apparatus according to claim 15, wherein the first photodetecting optical system is formed so that a first transforming device that divides reflected light reflected from the retina of the eye into at least seventeen light beams and a second transforming device that reduces the number of the light beams formed by the first transforming device can be inserted in an optical path thereof, the first state is set by inserting the first transforming device in the optical path and the second state is set by inserting the second transforming device at a position near the first transforming device in the optical path.

18. The eye characteristic measuring apparatus according to claim 15, wherein the first state is set by a first transforming device having apertures for transforming reflected light reflected from the retina of the eye into at least seventeen light beams, and the second state is set by inserting a mask that makes the reflected light pass the openings that are not adjacent to each other at a position near the first transforming device in an optical path of the first transforming device.

19. The eye characteristic measuring apparatus according to any one of claims 3, 4, 7 to 10, 12, 13 or 17, wherein the variable illuminating condition of the illuminating optical system is focusing condition for focusing the illuminating light on the retina of the eye, and the image forming condition that is changed by the image forming condition changing unit is condition of condensation of light that falls on the photodetecting device.

* * * * *